US006893854B2

(12) United States Patent
Janulaitis et al.

(10) Patent No.: US 6,893,854 B2
(45) Date of Patent: May 17, 2005

(54) NUCLEASE

(75) Inventors: Arvydas Janulaitis, Vilnius (LT); Renata Rimseliene, Vilnius (LT); Arvydas Lubys, Vilnius (LT)

(73) Assignee: Fermentas UAB, Vilnius (LT)

( * ) Notice: Subject to any disclaimer, the term of this patent is extended or adjusted under 35 U.S.C. 154(b) by 123 days.

(21) Appl. No.: 09/906,768

(22) Filed: Jul. 18, 2001

(65) Prior Publication Data

US 2003/0040614 A1 Feb. 27, 2003

(30) Foreign Application Priority Data

Aug. 10, 2000 (GB) ................................ 0019744

(51) Int. Cl.$^{7}$ ............................ C12N 9/22; C12N 15/55
(52) U.S. Cl. .................................... 435/199; 536/23.2
(58) Field of Search ........................ 435/199; 536/23.2

(56) References Cited

U.S. PATENT DOCUMENTS 6,413,758 B1 * 7/2002 Xu et al. ..................... 435/199

OTHER PUBLICATIONS

Roberts, et al. (2003) REBASE database, Eco57I, 6 pages.*
Janulaitis, A., et al. (1992) Nucl. Acids Res. 20(22), 6043–6049.*
Rimseliene, R. et al.: "Site–directed mutagenesis of type IV restriction endonuclease Eco57I" Biologija (1997) (1) 31–33.
Heitman J. et al.: "Mutants of the ECO–R–I Endonuclease with Promiscuous Substrate Specificity Implicate Residues Involved in substrate Recognition", EMBO (European Molecular Biology Organization) Journal 9:10 (1990) 3369–3378.
Petrusyte M. et al.: "Restriction Endonuclease of a New Type" Gene (Amsterdam) 74:1 (1988) 89–91.
Janulaitis. Arvydas et al.: "Cloning and sequence analysis of the genes coding for Eco571 type IV restriction–modification enzymes" Nucleic Acids Research 20:22 (1992) 6051–6056.
Alves J et al. (1989) "Changing the hydrogen–bonding potential in the DNA binding site of EcoRI by site–directed mutagenesis drastically reduces the enzymatic activity, not, however, the preference of this restriction endonuclease for cleavage within the site–GAATTC," Biochemistry 28: 2678–84.
Anderson J (1993) "Restriction endonucleases and modification methylases," Current Opinion in Structural Biology 3:24–30.
Cesnaviciene E et al. (2001) "Characterization of AloI, a restriction–modification system of a new type," J Mol Biol 314: 205–16.
Chandrasegaran S et al (1999) "Chimeric restriction enzymes: what is next?," Biol Chem 380: 841–8.

Dorner LF et al. (1999) "Genetic analysis of the base–specific contacts of BamHI restriction endonuclease," J Mol Biol 285: 1515–23.
Flores H et al. (1995) "Saturation mutagenesis of His114 of EcoRI reveals relaxed–specificity mutants," Gene 157: 295–301.
Geiger R et al. (1989) "Genetic engineering of EcoRI mutants with altered amino acid residues in the DNA binding site: physicochemical investigations give evidence for an altered monomer/dimer equilibrium for the Gln144Lys145 and Gin144Lys145Lys200 mutants," Biochemistry 28: 2667–77.
Gubler M et al (1992) "Recombination of constant and variable modules alters DNA sequence recognition by type IC restriction–modification enzymes," Embo J 11: 233–40.
Hager PW et al. (1990) "Probing the role of glutamic acid 144 in the EcoRI endonuclease using aspartic acid and glutamine replacements," J Biol Chem 265: 21520–6.
Jeltsch A et al. (1996) "Engineering novel restriction endonucleases: principles and applications," Trends Biotechnol 14: 235–8.
Jeltsch A et al. (1993) "Mutational analysis of the function of Gln115 in the EcoRI restriction endonuclease, a critical amino acid for recognition of the inner thymidine residue in the sequence –GAATTC– and for coupling specific DNA binding to catalysis," J Mol Biol 229: 221–34.
Kim YG et al. (1994) "Chimeric restriction endonuclease," Proc Natl Acad Sci U S A 91: 883–7.
Kim YG et al. (1998) "Chimeric restriction enzyme: Gal4 fusion to FokI cleavage domain," Biol Chem 379: 489–95.
Kim YG et al. (1996) "Hybrid restriction enzymes: zinc finger fusions to Fok I cleavage domain," Proc Natl Acad Sci U S A 93: 1156–60.
Kong H et al. (1994) "Characterization of Bcgl, a new kind of restriction–modification system," J Biol Chem 269: 683–90.

(Continued)

Primary Examiner—Charles L. Patterson, Jr.
(74) Attorney, Agent, or Firm—Pillsbury Winthrop LLP

(57) ABSTRACT

A process for producing a polynucleotide encoding a restriction endonuclease with an altered specificity, which process comprises:

(a) mutagenising a polynucleotide encoding a restriction endonuclease with specificity for a recognition sequence so as to produce one or more mutated polynucleotides; and
(b) isolating therefrom a polynucleotide encoding a mutated restriction endonuclease with specificity for an altered recognition sequence by selecting a polynucleotide which expresses a restriction endonuclease with methylase specificity for the altered recognition sequence.

21 Claims, 6 Drawing Sheets

OTHER PUBLICATIONS

Kumar S et al. (1994) "The DNA (cytosine–5) methyltransferases," *Nucleic Acids Res* 22: 1–10.

Lanio T et al. (1996) "EcoRV–T94V: a mutant restriction endonuclease with an altered substrate specificity towards modified oligodeoxynucleotides," *Protein Eng* 9: 1005–10.

Lanio T et al. (2000) "On the possibilities and limitations of rational protein design to expand the specificity of restriction enzymes: a case study employing EcoRV as the target," *Protein Eng* 13: 275–81.

Leung D (1989) "A method for random mutagenesis of a defined DNA segment using a modified polymerase chain reaction," *Technique, A Journal of Methods in Cell and Molecular Biology* (1) 1: 11–15.

Malone T et al. (1995) "Structure–guided analysis reveals nine sequence motifs conserved among DNA amino–methyltransferases, and suggests a catalytic mechanism for these enzymes," *J Mol Biol* 253: 618–32.

Meister J et al. (1993) "Microevolution by transposition: drastic modification of DNA recognition by a type I restriction enzyme following Tn5 transposition," *Embo J* 12: 4585–91.

OSuna J et al. (1991) "Combinatorial mutagenesis of three major groove–contacting residues of EcoRI: single and double amino acid replacements retaining methyltransferase–sensitive activities," *Gene* 106: 7–12.

Piekarowicz A et al. (1999) "The HaelV restriction modification system of *Haemophilus aegyptius* is encoded by a single polypeptide," *J Mol Biol* 293: 1055–65.

Schottler S et al. (1998) "Protein engineering of the restriction endonuclease EcoRV—structure–guided design of enzyme variants that recognize the base pairs flanking the recognition site," *Eur J Biochem* 258: 184–91.

Stemmer WP (1994) "DNA shuffling by random fragmentation and reassembly: in vitro recombination for molecular evolution," *Proc Natl Acad Sci U S A* 91: 10747–51.

Stemmer WP (1994) "Rapid evolution of a protein in vitro by DNA shuffling," *Nature* 370: 389–91.

Thielking V et al. (1991) "Site–directed mutagenesis studies with EcoRV restriction endonuclease to identify regions involved in recognition and catalysis," *Biochemistry* 30: 6416–22.

Timinskas A et al. (1995) "Sequence motifs characteristic for DNA [cytosine–N4] and DNA [adenine–N6] methyltransferases. Classification of all DNA methyltransferases," *Gene* 157: 3–11.

Vipond IB et al. (1996) "Random mutagenesis targeted to the active site of the EcoRV restriction endonuclease," *Biochemistry* 35: 1701–11.

Whitaker RD et al. (1999) "A mutant of BamHI restriction endonuclease which requires N6–methyladenine for cleavage," *J Mol Biol* 285 1525–36.

Yanofsky SD et al. (1987) "Clustering of null mutations in the EcoRI endonuclease," *Proteins* 2: 273–82.

Zhou YH et al. (1991) "Random mutagenesis of gene–sized DNA molecules by use of PCR with Taq DNA polymerase," *Nucleic Acids Res* 19: 6052.

* cited by examiner

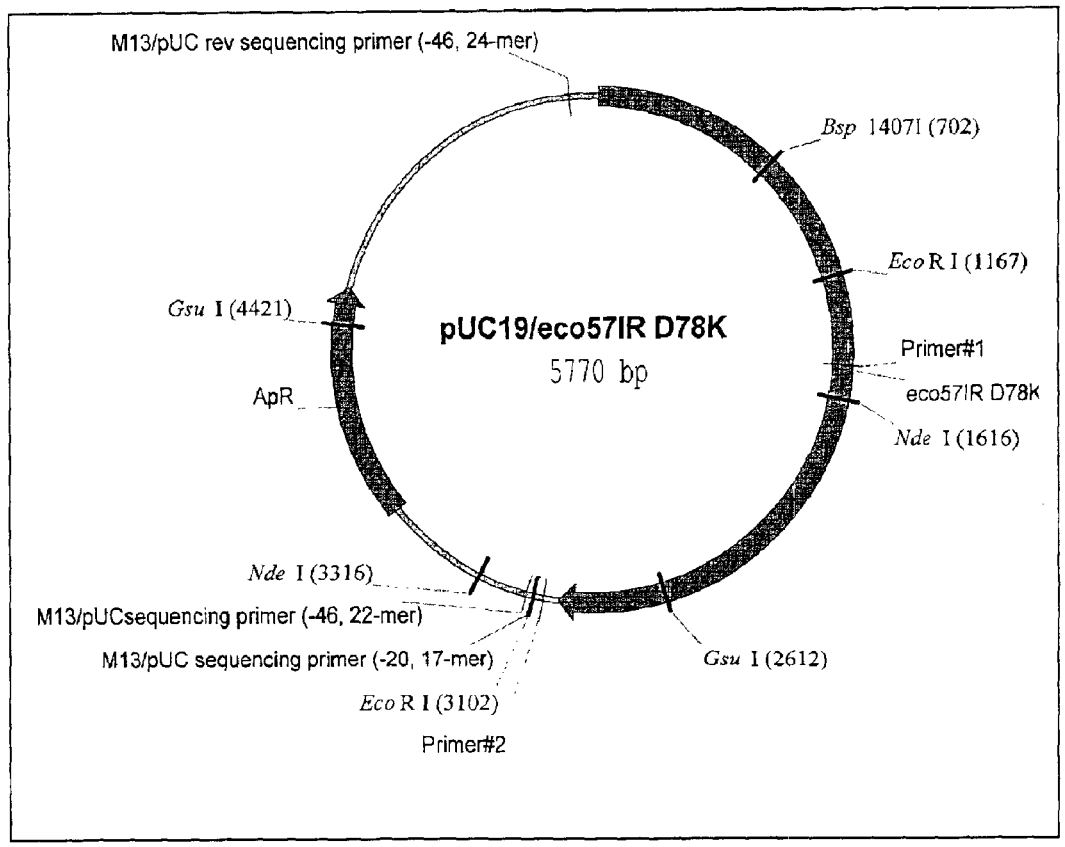
Fig. 1. Schematic representation of pUC19/eco57IR D78K plasmid. Binding sites of all primers used in PCR experiments are indicated in the picture.

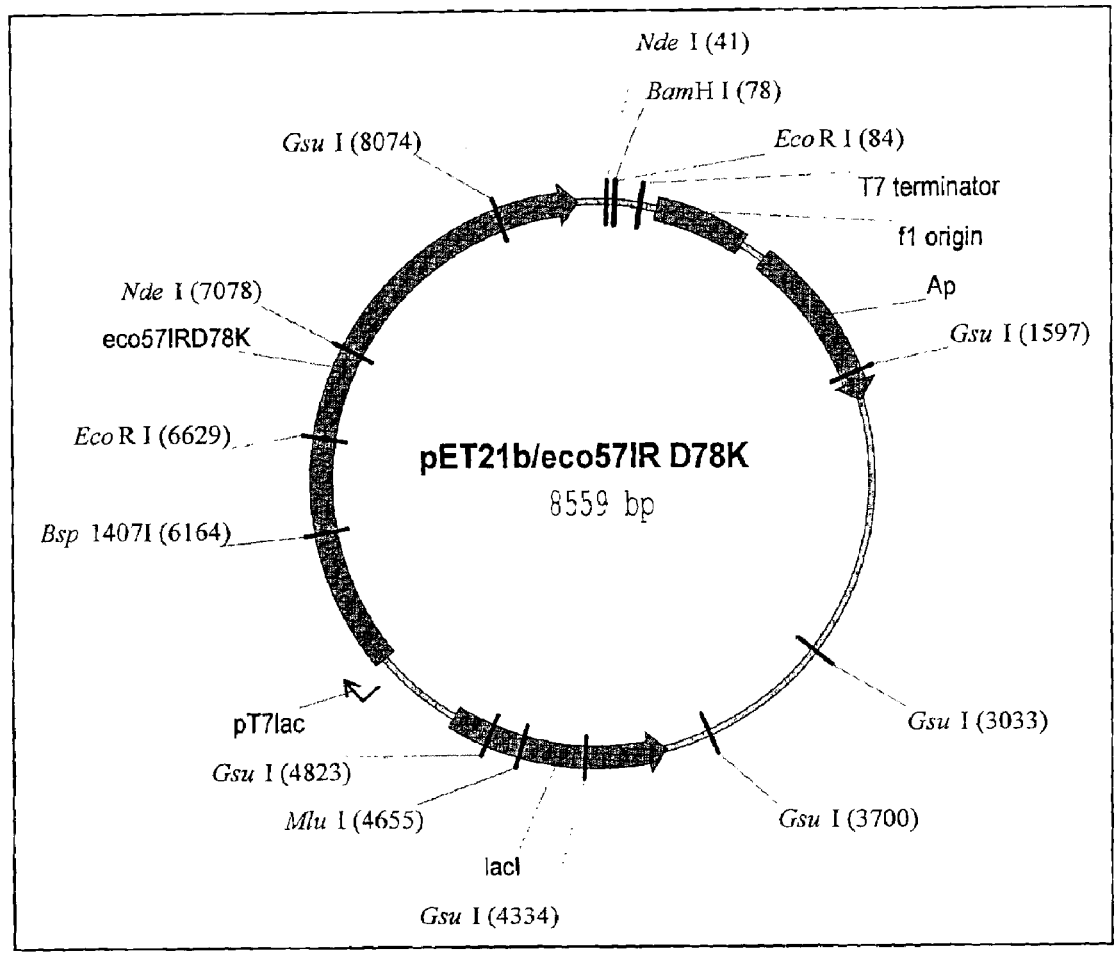
Fig. 2. Schematic representation of pET21b/eco57IR D78K plasmid.

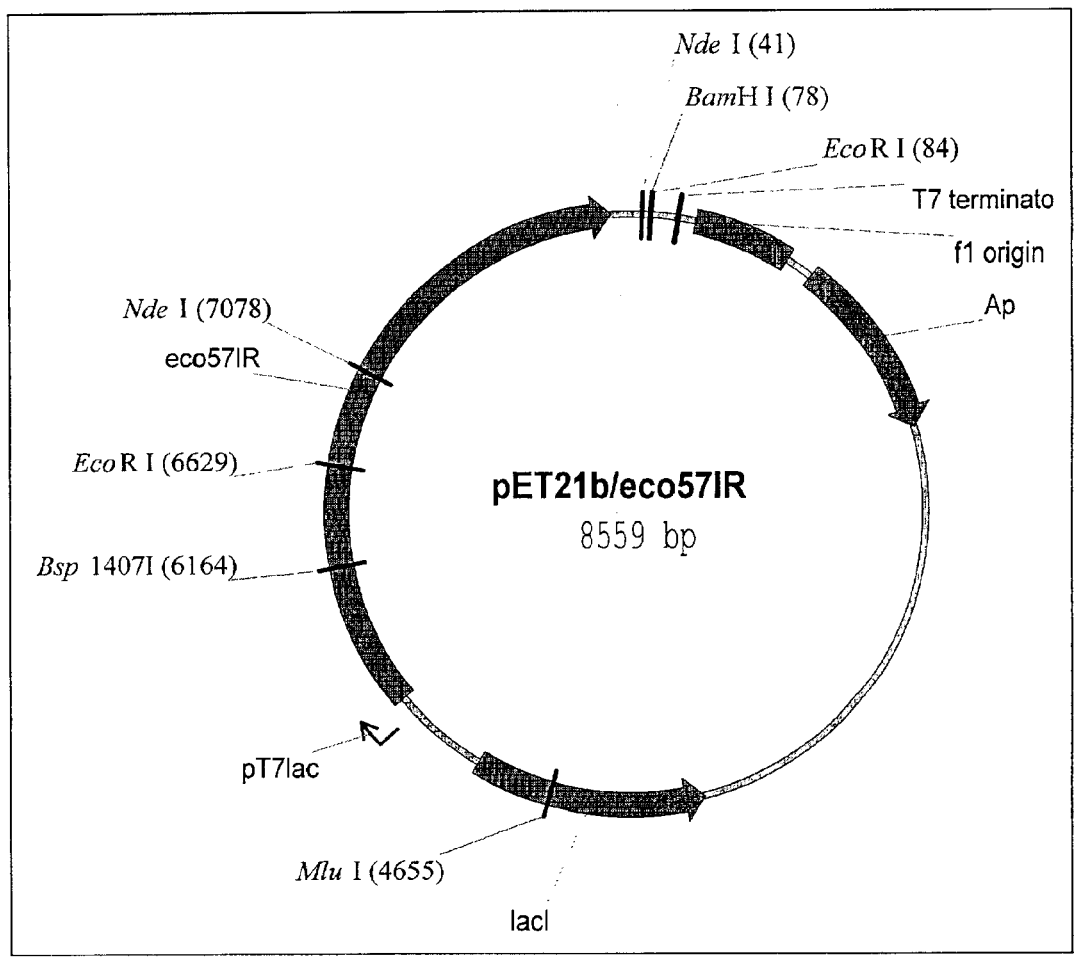
Fig. 3. Schematic representation of pET21b/eco57IR plasmid.

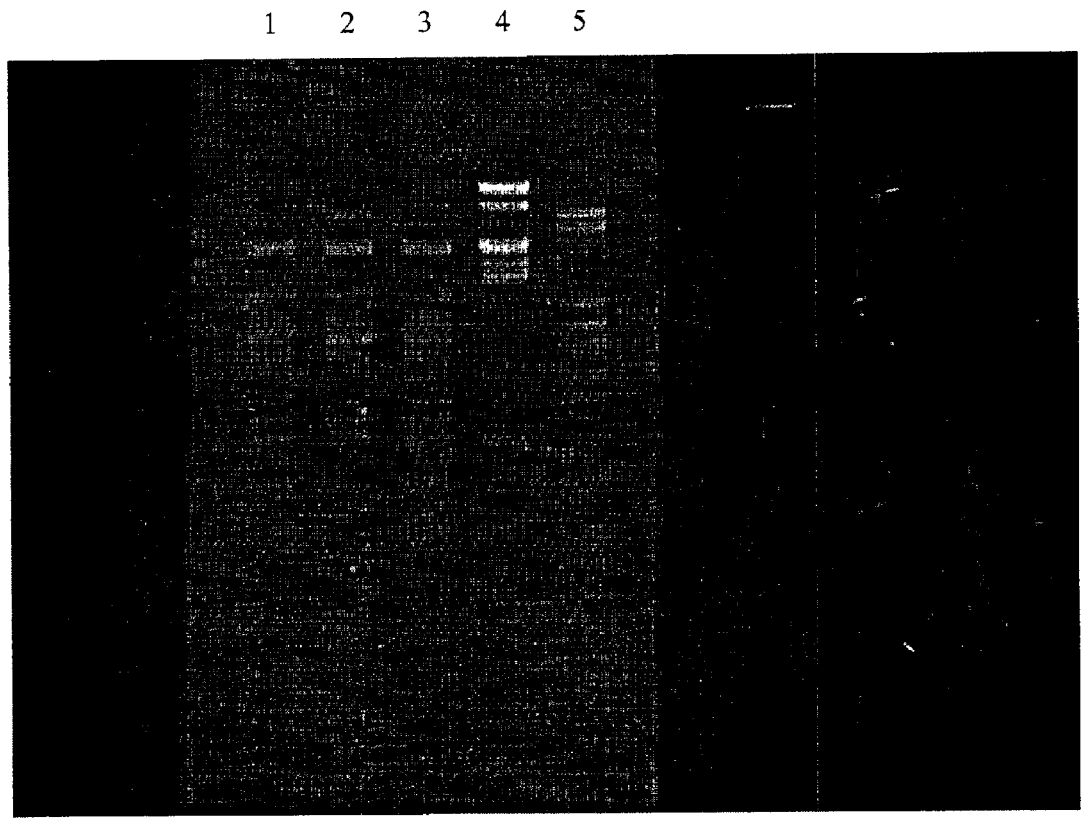
Fig. 4. Determination of substrate specificity of the Eco57I T862N mutant protein.
1. λ DNA digested with Eco57I+GsuI+Eco57I T862N
2. λ DNA digested with Eco57I T862N
3. λ DNA digested with Eco57I+GsuI
4. λ DNA digested with GsuI
5. λ DNA digested with Eco57I

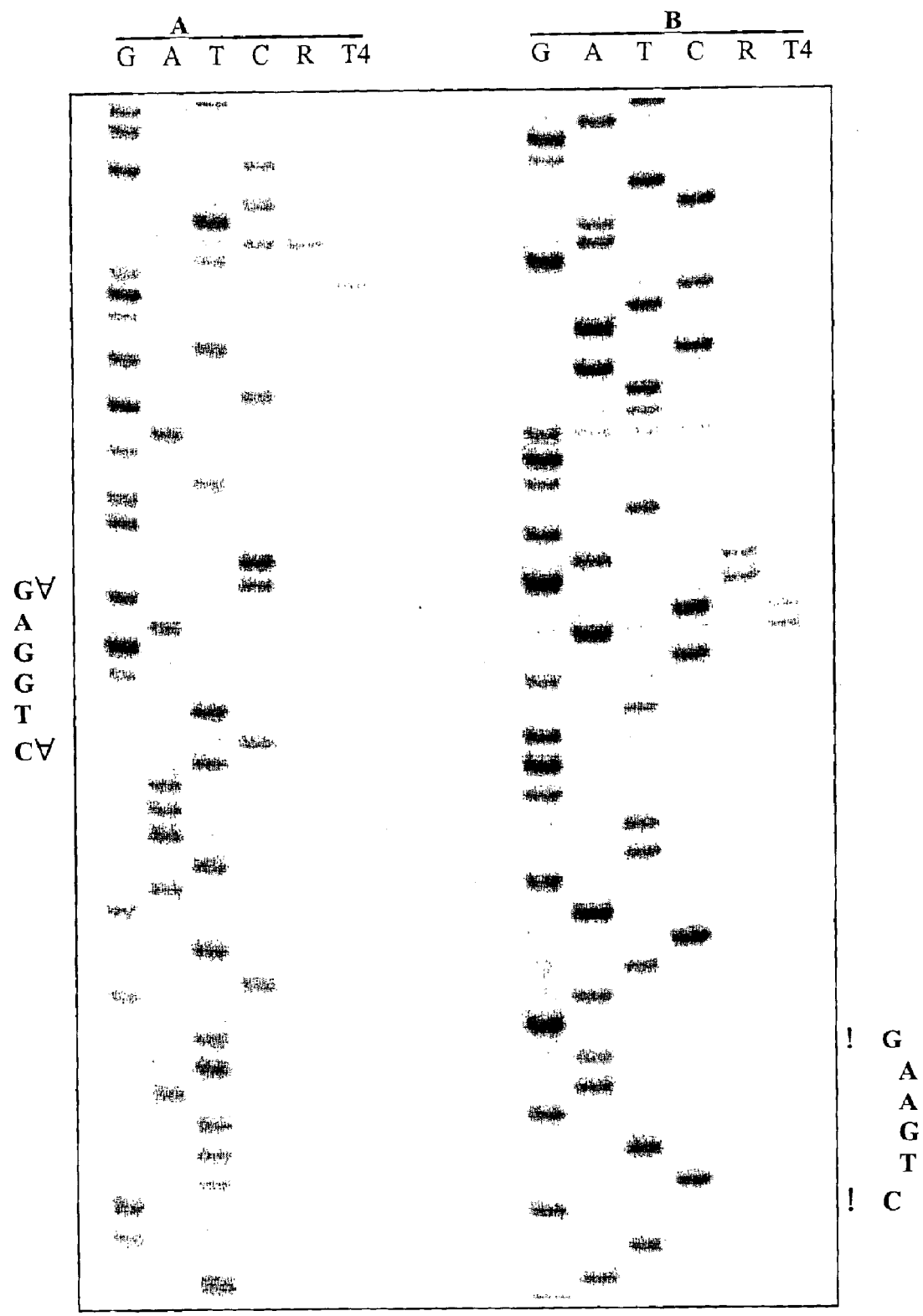
Fig. 5. A and B

GsuI site (position 454, bolded):
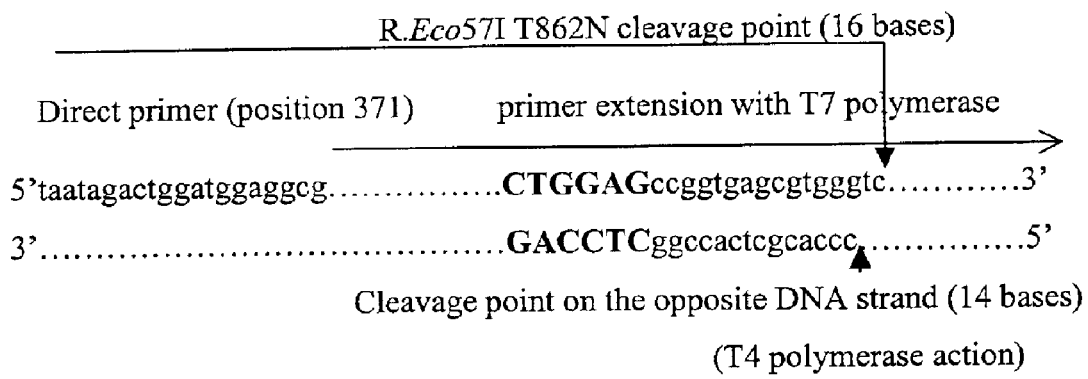
Eco57I site (position 3798, bolded):
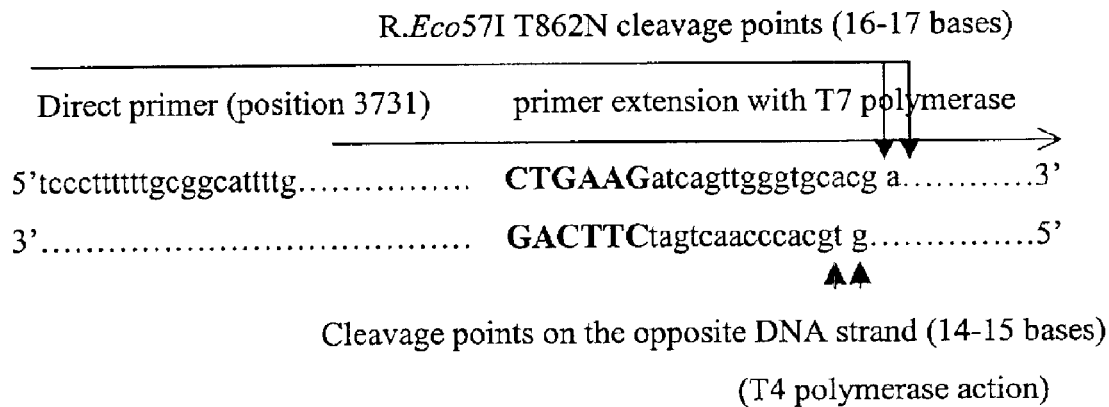
Fig. 5C

NUCLEASE

CROSS REFERENCE TO RELATED APPLICATIONS

This patent document is related to British Patent Application No. 0019744.2, filed Aug. 10, 2000, the content of which is incorporated herein by reference in its entirety.

The present invention relates to a restriction endonuclease, a polynucleotide encoding such a restriction endonuclease, and processes for the preparation of such restriction endonucleases and polynucleotides.

Restriction endonucleases cleave DNA with extremely high sequence specificity and due to this property they have become indispensable tools in molecular biology and molecular medicine. Despite the fact that several hundred different restriction enzymes have been isolated from various bacterial strains, many specificities are still unavailable. This situation and the growing need for wider selection of available restriction enzymes with differing recognition sequences has stimulated efforts to produce artificial restriction enzymes.

The specificity of a restriction enzyme may be defined by several components: the DNA sequence recognised by the enzyme, its mode of cleavage, and its sensitivity to DNA modifications within the recognition sequence. Sequences recognised by an enzyme's star activity as well as an enzyme's preferences for certain nucleotides flanking the recognition sequence may also be attributed to specificity phenomena. Attempts have been made to alter the specificity of restriction endonucleases, especially to change an enzyme's recognition sequence specificity. Although certain progress in this field has been achieved (1), experiments that sought the alteration of enzyme specificity for its recognition sequence by mutagenesis have been unsuccessful.

After the tertiary structures for EcoRI and EcoRV enzymes became available and specific amino acid residues that form specific contacts to the bases of the recognition sequence were identified, site-specific mutagenesis experiments were undertaken aimed at producing enzyme variants with new specificities by altering these contacts. However, extensive mutagenesis studies covering all the amino acid residues that form specific contacts to the bases of the recognition sequence, carried out with EcoRI ((2–8) and EcoRV (9, 10) revealed that none of the mutants had acquired a new specificity. Both by site—specific and saturating mutagenesis of residues involved in target recognition it was possible to produce some EcoRI and EcoRV mutants in which the coupling of recognition and catalysis is loosened, leading to a relaxed but not altered specificity of these mutants.

The same approach—rational protein design has been applied to engineering of restriction enzyme variants that attack modified substrates more readily than do the wild-type enzymes. This way, by eliminating one of the hydrophobic contacts between EcoRI and the methyl group of one thymine residue within its recognition sequence (GAA$\underline{T}$TC) it was possible to create an EcoRI variant that could not discriminate between thymine and uracil at this position (7). Similarly, two EcoRV mutants have been constructed (11), one cleaving a uracil-containing substrate more rapidly than wild type enzyme, and a second showing preference for a recognition sequence in which the GATATpC phosphate group is replaced by a methylphosphonate and hardly cleaving the unmodified substrate. A particular limitation of these newly created enzyme variants is that none of said substrate modifications occurs in native DNA, therefore these variants are unlikely to be useful as biochemical tools.

With a knowledge of tertiary enzyme structure protein engineering experiments were carried out to create enzymes that specifically recognise and cleave their recognition sequences when they are methylated. Site—specific mutagenesis of amino acid residues participating in DNA sequence recognition in BamHI catalytic centre resulted in BamHI variants which have lost their ability to cleave unmethylated GGATCC sequences by more than two orders of magnitude, while maintaining nearly wild-type levels of activity on the N6-methyladenine—containing sequence GGmATCC (12, 13). Random mutagenesis combined with genetic screen for relaxed specificity mutants of FokI restriction endonuclease resulted in isolation of FokI mutants capable to cleave hemimethylated FokI target sites in addition to those recognised by wild type enzyme (14).

Attempts based on site—directed mutagenesis have been undertaken to extend the specificity of restriction enzymes from six to eight, or even to ten base pairs by the creation of new base-specific contacts to base pairs that flank the recognition sequence. Several mutants of EcoRI and EcoRV have been created that differed in the cleavage rates of recognition sites with different flanking sequences much more than the wild type enzymes. After comparison of the cleavage rates of two EcoRV sites located in a different sequence context, which are cleaved at equal rates by the wild type enzyme, it was possible to identify EcoRV mutants that cleaved a site flanked by AT-rich sequences up to one order of magnitude more readily than a site flanked by GC-rich sequences (15, 16). Although EcoRV mutant variants showed more significant site preferences than the wild type enzyme, all attempts to alter restriction enzyme specificity from six nucleotides to eight were unsuccessful. Experimental data demonstrate that even for the very well characterized restriction enzyme, such as EcoRV, the properties that determine specificity and selectivity are difficult to model on the basis of the available structural information, constituting this way the main limitation of all experiments based on rational protein design.

Another approach has been applied in experiments attempting to alter specificity of type IIS and type I restriction endonucleases. As these enzymes are composed of different domains or subunits, one of which is responsible for sequence specificity and another for catalysis, these enzymes are good targets for domain and subunit-swapping experiments in an attempt to transplant the specificity of one enzyme onto another one. Such experiments are quite successful. For example, by fusing the N-terminal half of the recognition subunit hsdS of the type I restriction enzyme StyR124I recognising sequence GAAN$_6$RTCG (SEQ ID NO: 1) with the C-terminal half of the hsdS subunit of EcoDXXI, which has the recognition sequence TCAN$_7$RTTC (SEQ ID NO: 2), a hybrid enzyme was obtained that had a new intermediate specificity GAAN$_6$RTTC (SEQ ID NO: 3) (17). Transposon mutagenesis applied for EcoDXXI resulted in creation of novel mutant in which the specificity has been altered due to a Tn5 insertion into the middle of hsdS gene into an interrupted palindrome, TCAN$_8$TGA (SEQ ID NO: 4), in which the 5' half site of the wild type site is repeated in inverse orientation (18).

Series of experiments performed by fusing DNA binding domains of several proteins to the cleavage domain of FokI restriction endonuclease resulted in creation of chimeric restriction endonucleases that cleave DNA at sites recognised by fused DNA binding domain (19–22).

All rational protein design experiments aiming to generate restriction enzymes with new specificities that were based on site-specific mutagenesis did not achieve the desired goal probably because the recognition of individual base pairs is determined by interactions with multiple amino acid residues and changes in specificity might require the simultaneous exchange of several amino acid residues at the protein-DNA interface.

The applicants have recognised that whilst a random mutagenesis approach has hitherto been applied (5, 12, 13, 14, 23, 24) to solve the problem of generating restriction enzymes with new specificities, this approach is quite limited in the absence of a useful selection method for the desired restriction enzyme.

The present invention now provides a process for producing a polynucleotide encoding a restriction endonuclease with an altered specificity, which process comprises:

(a) mutagenising a polynucleotide encoding a restriction endonuclease with specificity for a recognition sequence so as to produce one or more mutated polynucleotides; and (b) isolating therefrom a polynucleotide encoding a mutated restriction endonuclease with specificity for an altered recognition sequence by selecting a polynucleotide which expresses a restriction endonuclease with methylase/specificity for the altered recognition sequence.

The process of the present invention includes a powerful selection method for use in isolating restriction endonucleases with new specificities. This selection method exploits the ability of certain restriction endonucleases to exhibit methylation activity towards the recognition sequence in addition to the restriction endonuclease activities of sequence recognition and cleavage. In particular, selection of a polynucleotide which expresses a restriction endonuclease with altered recognition sequence methylase specificity can be carried out by cleaving the products of mutagenesis step (a), comprising mutated polynucleotides and wild-type polynucleotides, which have an unaltered recognition sequence methylase specificity. The polynucleotide is preferably DNA.

In a first embodiment the restriction endonuclease has methylase activity towards a target base in the recognition sequence and the altered recognition sequence comprises the recognition sequence altered in at least one nucleotide base.

In this embodiment there is therefore provided a process for producing a polynucleotide encoding a restriction endonuclease with an altered specificity, which process comprises:

(a) mutagenising a polynucleotide encoding a restriction endonuclease so as to produce a polynucleotide library comprising mutated polynucleotides, which restriction endonuclease has specificity for a recognition sequence and methylase activity towards a target base in the recognition sequence;

(b) incorporating each mutated polynucleotide into a polynucleotide vector to form a vector library, wherein the polynucleotide vector has a sub-sequence comprising an altered sequence which comprises the recognition sequence altered in at least one nucleotide base, and a selection sequence overlapping the altered sequence to an extent which includes the target base;

(c) propagating the vector library to form a propagated library under conditions to permit restriction endonuclease catalysed polynucleotide methylase activity;

(d) treating the propagated library with a selection restriction endonuclease with specificity for the selection sequence and sensitivity to methylation in the selection sequence to cleave polynucleotides containing unmethylated selection sequences; and (e) isolating therefrom an uncleaved polynucleotide encoding a restriction endonuclease with specificity for the altered sequence.

The restriction endonuclease to be mutagenised may be any suitable enzyme which additionally has methylase activity, preferably in the presence of S-adenosyl methionine so that the recognition sites in the vector, such as a plasmid vector carrying the gene for such a restriction endonuclease, are resistant at least to some extent to their own cleavage in vitro even without a gene for cognate DNA methylase being present in the host cell. Suitable endonucleases include those of type IV, such as Eco57I (25, 26) or GsuI (27, 28). In enzymes of this type, mutations in the polynucleotide encoding the restriction endonuclease can affect both methylase and endonuclease specificity. Enzymes like this which cleave at their recognition sequence are good candidates for use in the process of the present invention. Other candidates include type I or type III restriction enzymes; and those type II restriction enzymes which contain in their amino acid sequence one or more motifs characteristic of a DNA methyltransferase. Such type II enzymes include BcgI-type enzymes (29), HaeIV-type enzymes (30), AloI-type enzymes (31) and CjeI type enzymes.

The polynucleotide encoding the restriction endonuclease may be wild-type or may be itself a mutant variant including those enzymes which possess endonuclease activity and have had their methylation activity restored (see below), and enzymes which favour cleavage over methylation such as Eco57I. In enzymes of the latter class, it is possible to use cleavage-deficient mutants as described in the specific description below as targets for mutagenesis and subsequently reconstitute cleavage activity to produce an altered restriction endonuclease in accordance with the present invention.

The selection restriction endonuclease can also be any suitable restriction endonuclease provided that it is sensitive to methylation in the selection sequence and has a selection sequence (i.e. its own recognition sequence) which overlaps the altered sequence to an extent which includes the target base. This is a preferred means by which selection of the altered recognition sequence methylase/specificity in the mutant restriction endonuclease can be achieved. As set out in the specific examples herein, the selection sequence may overlap the altered sequence by a single base or by all bases, as in the case of Eco57I and GsuI. It is preferred that there is at least a two base overlap, more preferably at least a three base overlap. Overlap may also arise within a recognition sequence, as in the case with AloI which has the recognition sequence GGANNNNNNGTTC (SEQ ID NO: 5) (in which the A is the target base for methylase activity).

The precise method of mutagenesis is not critical to the invention and may be site-specific or random mutagenesis. The method of mutagenesis chosen will depend upon the need of any particular experimental protocol. Methods include use of mutagenic polymerase chain reaction (PCR), chemical mutagenesis, DNA shuffling and the use of a mutator host strain. The present invention is able to use non-specific or random mutagenesis methods because of the use of a powerful selection method to isolate mutant polynucleotides encoding desirable restriction endonuclease.

Once mutagenesis has taken place, each mutated polynucleotide may be incorporated into a polynucleotide vector by any conventional method. Any conventional vector such as a suitable cloning plasmid vector may be used provided that the vector has a sub-sequence comprising the altered sequence and a selection sequence overlapping the altered sequence as required herein. It is preferred that a plurality of such sub-sequences are present in the vector to achieve improved selection. The vector library may be propagated by any conventional method such as by transforming a suitable host such as a bacterial cell and growing the host in an appropriate growth medium. The bacterial cell may be a suitable strain of *E. coli*. The conditions under which the vector library is propogated must be such as to permit restriction endonuclease catalysed polynucleotide methylase activity. This methylase activity is required so as to permit methylation of the recognition sequences of the restriction endonucleases encoded by the vector library members. This would normally be the case on propagation of a host cell such as *E. coli*.

In the step of treating the propagated library with a methylation sensitive selection restriction endonuclease, the aim is to cleave all polynucleotides containing unmethylated selection sequences so as to leave behind only those restriction endonucleases which successfully methylated the altered sequence as provided by the polynucleotide vector. It is preferred that this step is carried out on the propagated library after the library has been isolated from host cells. Whilst individual members could be treated in this way, it is advantageous for the propagated library to be pooled. Transformed host cells containing members of the propagated library therefore need not be grown individually but can themselves also be pooled or grown together.

The step of isolating from the treated propagated library an uncleaved polynucleotide is conveniently based on the significantly decreased transformation efficiency of cleaved polynucleotides to transform host cells such as bacteria. Other conventional methods are possible, including size-based separation of the uncleaved polynucleotides. During isolation of the uncleaved polynucleotide, it is convenient for this to be amplified either whilst present in the vector or following excision therefrom. Amplification of the uncleaved polynucleotide may be effected by any conventional means. Amplification is conveniently achieved by transformation of a host cell, propagation of that host cell and subsequent isolation therefrom of the uncleaved polynucleotide within the vector. The uncleaved polynucleotide would be expected to encode a mutant restriction endonuclease. Where a number of transformants are produced according to this method, the vectors, such as plasmid DNA, from the transformants may be individually analysed by conventional methods to determine sequence information and restriction mapping behaviour of the mutant restriction endonucleases obtained thereby.

In a second embodiment of the present invention a method is provided whereby certain methylase deficient restriction enzymes can be used as target enzymes for mutagenesis by firstly restoring their methylase activity. In this embodiment, the restriction endonuclease is prepared by (a) selecting a methylase-deficient restriction endonuclease which has in its amino acid sequence a motif characteristic of a DNA methyltransferase; and (b) restoring methylase activity in the methylase deficient restriction endonuclease.

Preferably, the step of restoring the methylase activity comprises:

(a) mutagenising a polynucleotide encoding the methylase-deficient restriction endonuclease so as to produce a polynucleotide library comprising mutated polynucleotides, which restriction endonuclease has specificity for a recognition sequence;

(b) incorporating each mutated polynucleotide into a polynucleotide vector to form a vector library, which polynucleotide vector has the recognition sequence;

(c) propagating the vector library to form a propagated library under conditions to permit restriction endonuclease catalysed polynucleotide methylase activity;

(d) treating the propagated library with a restriction endonuclease with specificity for the recognition sequence to cleave polynucleotides containing an unmethylated recognition sequence; and (e) isolating therefrom an uncleaved polynucleotide encoding a restriction endonuclease with methylase activity.

This process of restoring methylase activity operates in much the same way as the process for producing a polynucleotide encoding a restriction endonuclease with altered sequence specificity. Accordingly, the comments set out above particularly in relation to steps of mutagenising the polynucleotide and incorporating the mutated polynucleotide into a vector, propagating the vector library and finally isolating a desired restriction endonuclease therefrom apply equally here. The difference in the process arises from a different selection procedure for cleaving unwanted products of mutagenesis.

The method for cleaving unwanted mutagenesis products requires the activity of a restriction endonuclease with specificity for the recognition sequence to cleave those recognition sequences which are unmethylated. This is conveniently provided by the methylase deficient restriction endonuclease itself. By cleaving unmethylated recognition sequences, only those mutagenesis products encoding restriction endonucleases with restored methylase activity will be protected against cleavage.

Motifs characteristic of DNA methylases would be known to the skilled reader and typical examples are discussed in references 39 to 41.

The present invention will now be described in further detail, by way of example only, with reference to the accompanying drawings in which:

FIG. 1 shows a schematic representation of a pUC 19/eco57IR D78K plasmid;

FIG. 2 shows a schematic representation of a pET2 1b/eco57IR D78K plasmid;

FIG. 3 shows a schematic representation of a pET2lb/eco57IR plasmid;

FIG. 4 shows the results of agarose gel electrophoresis in determining substrate specificity of the Eco57I T862N mutant protein; and FIG. 5 shows the results of determining the Eco57I T862N cleavage site in a sequencing gel (A and B) and schematically (C) (SEQ ID) NOS: 48–51). The top portion of FIG. 5C schematically shows the site at which Eco57I T862N cleaves relative to the GsuI recognition site (bolded), the 5' nucleotide of which is at position 454. The bottom portion of FIG. 5C schematically shows the site at which Eco57I T862N cleaves relative to the Eco57I recognition site (bolded), the 5' nucleotide of which is at position 3798.

EXAMPLES

Construction of Eco57I Mutant Variant with Altered Specificity

Eco57I restriction endonuclease is a bifunctional enzyme, which not only recognizes and cleaves DNA sequence CTGA$\underline{A}$G(N)$_{16/14}$ ↓ (SEQ ID NO: 6), but also methylates the second adenine within its recognition sequence (underlined) in the indicated DNA strand. Studies of Eco57I restriction endonuclease amino acid sequence revealed two sequence motifs 77PDX$_{13}$EXK (SEQ ID NO: 7) and 81 IRKX20DXk (SEQ ID NO: 8) that are reminiscent of the catalytic/Mg$^{2+}$ binding sites identified in some restriction endonucleases (32). Site directed mutagenesis experiments performed on both putative catalytic centres of Eco57I restriction endonuclease have demonstrated that D78N, D78A, D78K mutations completely abolish the cleavage activity while retaining the methylation activity of restriction enzyme (33).

Eco57I rather cleaves than methylates its recognition sequence, therefore the gene for this restriction endonuclease is lethal for the host cell when introduced without cognate DNA methyltransferase. Since the mutant variants of this enzyme deficient in DNA cleavage and proficient in methylation of their recognition sequence were available at the time of conception of present invention these mutants were chosen as a model object to reduce the invention to practice. However, it is not always necessary to create cleavage deficient mutants to practice the disclosed invention. Due to unique structure of encoded protein genes for the following Type II restriction endonucleases are non lethal to the host cells: BcgI, HaeIV, AloI (34), therefore selection for altered specificity of these enzymes according to disclosed method may be performed directly using the gene for the wild type enzyme.

GsuI restriction endonuclease recognises DNA sequence CTGGAG(N)16/41 ↓(SEQ ID NO: 9), that differs in one nucleotide from that of Eco57I and is sensitive to the methylation of adenine in the indicated strand. Plasmids overproducing mutant version of Eco57I D78K are protected from cleavage with Eco57I, while they are sensitive to GsuI cleavage. Thereby, GsuI restriction endonuclease is a good candidate to enrich and screen DNA libraries with eco57IR D78K mutagenized gene for the new specificity.

For a mutagenesis experiment, a gene encoding Eco57I D78K mutant protein was subcloned into pUC19 cloning vector, yielding this way plasmid pUC19/eco57IR D78K (FIG. 1). In parallel, plasmid pET21b/eco57IR D78K (FIG. 2) was constructed where the same gene was inserted into pET21b expression vector in the orientation coinciding with that of transcription from T7 promoter.

Plasmid pUC19/eco57IR D78K was used as a substrate for error-prone mutagenic PCR with standard M13/pUC direct (−46, 22-mer) and reverse (−46, 24-mer) sequencing primers (MBL Fermentas). 0.2 μM of each primer and 0.1 μg of plasmid DNA were taken into reaction and several mutagenic error-prone PCRs were performed as described in Leung et al. and Zhou et al. (35, 36). 3.2 kb DNA fragments obtained in all mutagenic PCRs were combined together and agarose gel purified using DNA Extraction Kit (MBI Fermentas). 3.2 kb DNA fragments obtained in all mutagenic PCRs were subjected further to DNA shuffling as described in Stemmer et al. (37, 38). About 2 μg of gel purified 3.2 kb PCR fragment were incubated with 1 ng of DNAse I (Sigma) in the reaction buffer: 50 mM Tris-HCl pH7.4, 100 mM MnCl2, at 30° C. for time points from 5 to 20 mm. Degraded DNA fragments ranging from 50 to 500 bp were subsequently purified from agarose gel and taken into a self-assembly PCR reaction with no primers. All attempts to reassembly 3.2 kb PCR product were unsuccessful and resulted in a smeared DNA product that was somewhat smaller in size that 3.2 kb. Therefore this DNA was reamplified by nested PCR using M13/pUC seqencing primer and Primer#1, that annealed to the DNA sequence of eco57IR gene (see FIG. 1, positions 1495–1524).

Primer#1: 5'GCTTGATAGATAGTGGAGACAAAGT-TAAAC3' (SEQ ID NO: 10)

The obtained 1.6 kb PCR fragment was reamplified once more using Primer#1 and Primer#2 having introduced BamHI site that annealed downstream the termination codon of eco57IR gene (positions 3065–3087 in FIG. 1).

Primer#2: 540 GTAAGTAGGGATCCAAAAGTCGG3' (SEQ ID NO: 11) (BamHI site is underlined)

Following gel purification 1.6 kb PCR fragment was digested with NdeI-BamHI and a 1.5 kb DNA fragment encompassing the C-terminal part of eco57IR gene was agarose gel purified. The fragment was ligated with NdeI-BamHI digested and gel-purified pET21b/eco57IR D78K so as to substitute the wild type C-terminal portion of eco57IR gene with the mutagenized one. E. coli ER2566 cells were subsequently transformed with the ligation mixture by electroporation yielding this way a library of approximately 300,000 clones of eco57IR D78K gene mutants. All transformants after plating on ampicillin and IPTG (100 μM) were incubated overnight at 37° C. and for another 24 hours at room temperature to ensure higher levels of expression of Eco57I mutant proteins, that should result in higher levels of methylation of plasmids encoding said proteins. Afterwards all transformants were pooled, total plasmid DNA was isolated and subjected to digestion with GsuI. Plasmid pET21b/eco57IR D78K has six recognition sites for GsuI, five of them originating from the vector molecule (see FIG. 2). Therefore all plasmids where GsuI recognition sequences are non-methylated were fragmented. The only plasmids that could survive the GsuI digestion should be the ones where GsuI recognition sequences become methylated due to the altered specificity of Eco57I D78K protein. E. coli ER2566 cells were subsequently transformed with a digestion mixture by standard $CaCl_2$ transformation techniques and plated on ampicillin, IPTG (100 μM) plates. Individual plasmid DNAs were isolated from about 100 transformants obtained thereby and subjected to restriction endonuclease mapping. A restriction map of eleven plasmids coincided with that of pET21b/eco57IR D78K and all of them when isolated from IPTG induced cells were to a certain extent protected from both GsuI and Eco57I cleavage. These data suggest that these plasmids encode Eco57I D78K mutant variant with the new specificity 5' CTGPuAG3'.

Seven plasmids were sequenced in order to deduce what type of mutations result in the alteration of Eco57I specificity. According to sequencing data all mutant proteins could be grouped into four types:

1. T862N (one clone)
2. Q777R, T862S (one clone)
3. E673, N720, T862S (four clones)
4. E673G, N720D, K770N, T862S (one clone)

Sequencing results indicate that all mutant variants had the substitution of threonine at the position 862, that should be the only substitution in all cases responsible for altered specificity. In order to test that selected mutant variants of Eco57I exhibit not only altered specificity of methylation, but altered cleavage activity as well, the latter has been restored in the mutant variant with single mutation T862N. For this purpose 1509 bp DNA fragment excised with MluI-Bspl407I from plasmid pET21b/eco57IR D78K T862N was substituted by the same fragment from the plasmid pET21b/eco57IR encoding the wild type eco57IR gene (FIG. 3). E. coli ER2566 cells containing both gsuIM and eco57IM genes provided on compatible plasmids were transformed with ligation mixture and transformants were analysed by restriction mapping with TatI having an additional recognition site overlapping the D78K mutation. Restriction endonuclease activity was detectable in the crude cell extracts prepared from IPTG induced cells carrying plasmid where the cleavage domain of Eco57I T862N mutant variant has been restored. Eco57I T862N mutant and double mutant Eco57I D78K T862N proteins were isolated and purified in order to determine more precisely their biochemical properties.

Purification of Eco57I Mutant Proteins

Recombinant plasmids that were used for overexpression of Eco57I T862N and Eco57I D78K T862N mutant proteins, pET21b/eco57IR T862N and pET21b/eco57IR D78K T862N (see FIG. 2; restriction maps of both plasmids are identical except an additional TatI recognition site in pET21b/eco57IR D78K T862N that overlaps D78K), employed an inducible T7 promoter expression system. A sample of *E. coli*; ER 2566 transformed with plasmids pET21b/Eco57IRT 862N, pACYC184-GsuIM, pKpnORI-Km-Eco57IM was deposited at the Microbial Strain Collection of Latvia, blvd Kronvalda 4, Riga, LV-1586 under accession number 640.

Induction scheme for said proteins was as follows: *E. coli* ER2566 cells were transformed with relevant overexpressing plasmids. In the case of pET21b/eco57IR T862N host cell DNA was pre-methylated by introducing both gsuIM and eco57IM genes on compatible plasmids prior to transformation. Transformants were cultivated overnight in liquid LB medium supplemented with ampicillin (50 mg/l) at 37° C. The overnight culture was added to fresh LB medium supplemented with ampicillin (50 mg/l) and propagated at 37° C. till mid log phase ($OD_{600}$=0.7). IPTG was then added to the 500 μM final concentration and cultivation was carried out at 30° C. for another 4 hours. The cells then were harvested by centrifugation and proteins were purified as follows:

1. Purification of Eco57I T862N mutant protein: All the following procedures were performed either on ice or at 4° C. Cell biomass was resuspended in Buffer A (10 mM $K_2HPO_3$ pH 7.0, 1 mM EDTA, 7 mM 2-mercaptoethanol) supplemented with 300 mM NaCl at the ratio 4 ml buffer/1 g cell biomass and broken by sonication (22 kHz, 100W) for 5–8 min./100 ml suspension. Nucleic acids were eliminated by addition to sonicated suspension of poliethylenimine to 1% final concentration and by centrifugation at 10,000 rpm (Beckman JA10 rotor) for 10 min. Supernatant was collected and dry ammonium sulphate was added while slow mixing to 60% saturation. Proteins were precipitated by centrifugation at 10,000 rpm (Beckman JA10 rotor) for 10 min and collected pellet was dissolved in Buffer A supplemented with 200 mM NaCl at the ratio 1–2 ml/1 g pellet. Protein suspension was then dialyzed against 30–50 times higher volume of Buffer A supplemented with 200 mM NaCl. Resulting protein extract was then loaded onto a phosphocellulose P11 (Whatman) column equilibrated with Buffer A supplemented with 200 mM NaCl at the ratio 2–4 ml sorbent/1 g cell biomass. The column was washed with two column volumes of Buffer A supplemented with 200 mM NaCl and a linear gradient of ten column volumes from 0.2M to 1M of NaCl dissolved in Buffer A was applied with the flow speed 10 ml/cm² per hour. The enzyme eluted at 0.29–0.4M NaCl and was pooled. Pooled fractions were then dialyzed against 20–30 times higher volume of Buffer A overnight and loaded onto a Q Sepharose (Amersham Pharmacia Biotech) column equilibrated with Buffer A at the ratio 0.5–0.9 ml sorbent/1 g cell biomass. The column was washed with two column volumes of Buffer A and a linear gradient of ten column volumes from 0.0 M to 0.3M of NaCl dissolved in Buffer A was applied with the flow speed 10 ml/cm² per hour. The enzyme eluted at 0.165–0.19M NaCl and was pooled. Pooled fractions were then dialyzed against 20–50 times higher volume of Buffer A supplemented with 100 mM NaCl overnight and loaded onto a Blue Sepharose (Amersham Pharmacia Biotech) column equilibrated with Buffer A supplemented with 100 mM NaCl at the ratio 0.3–0.8 ml sorbent/1 g cell biomass. The column was washed with two column volumes of Buffer A supplemented with 100 mM NaCl and a linear gradient of ten column volumes from 0.1M to 0.7M of NaCl dissolved in Buffer A was applied with the flow speed 10 ml/cm² per hour. The enzyme eluted at 0.44–0.57M NaCl and was pooled. Pooled fractions were then dialyzed against 20–50 times higher volume of Buffer A overnight and loaded onto a DEAE-52 Cellulose (Whatman) column equilibrated with Buffer A at the ratio 0.3–0.8 ml sorbent/1 g cell biomass. The column was washed with two column volumes of Buffer A and a linear gradient of ten column volumes from 0.0M to 0.3M of NaCl dissolved in Buffer A was applied with the flow speed 10 ml/cm² per hour. The enzyme eluted at 0.06–0.1M NaCl, was pooled and immediately loaded onto a hydroxyl apatite (Calbiochem) column equilibrated with Buffer A supplemented with 100 mM NaCl at the ratio 0.3–0.8 ml sorbent/1 g cell biomass. The column was washed with two column volumes of Buffer A supplemented with 100 mM NaCl and a linear gradient of ten column volumes from 0.01M to 0.2M of NaCl dissolved in Buffer A was applied with the flow speed 10 ml/cm² per hour. The enzyme eluted at 0.11–0.16M NaCl and was pooled. Pooled fractions were then dialyzed against 10–20 times higher volume of Storage Buffer (10 mM $K_2HPO_4$ pH 7.4, 100 mM NaCl, 1 mM EDTA, 7 mM 2-mercaptoethanol, 50% v/v glycerol). The above purification scheme yielded apparently homogenous protein preparation with the molecular weight of about 108 kDa as confirmed by Coomasie blue R-250 stained SDS-PAGE gel electrophoresis. Protein concentration was measured according to Bradford and was found to be 0.5 mg/ml with specific activity 2 u/μg of protein when expressed in restriction endonuclease activity units (determined as described in MBI Fermentas Catalogue).

2. Purification of Eco57I D78K T862N mutant protein: All the following procedures were performed either on ice or at 4° C. Cell biomass was resuspended in Buffer A (10 mM $K_2HPO_3$ pH 7.0, 1 mM EDTA, 7 mM 2-mercaptoethanol) supplemented with 200 mM NaCl at the ratio 4 ml buffer/1 g cell biomass and broken by sonication (22 kHz, 100W) for 5–8 min./100 ml suspension. Nucleic acids were eliminated by addition to sonicated suspension of polyethylenimine to 1% final concentration and by centrifugation at 10,000 rpm (Beckman JA10 rotor) for 10 min. Supernatant was collected and dry ammonium sulphate was added while slowly mixing to 60% saturation. Proteins were precipitated by centrifugation at 10,000 rpm (Beckman JA10 rotor) for 10 min and collected pellet was dissolved in Buffer A supplemented with 200 mM NaCl at the ratio 1–2 ml/1 g pellet. Protein suspension was then dialyzed against 30–50 times higher volume of Buffer A supplemented with 200 mM NaCl. Resulting protein extract was then loaded onto a phosphocellulose P11 (Whatman) column equilibrated with Buffer A supplemented with 200 mM NaCl at the ratio 2–4 ml sorbent/1 g cell biomass. The column was washed with two column volumes of Buffer A supplemented with 200 mM NaCl and a linear gradient of ten column volumes from 0.2M to 1M of NaCl dissolved in Buffer A was applied with the flow speed 10 ml/cm² per hour.

The enzyme eluted at 0.29–0.37M NaCl and was pooled. Pooled fractions were then dialyzed against 20–30 times higher volume of Buffer A overnight and loaded onto a Q Sepharose (Amersham Pharmacia Biotech) column equilibrated with Buffer A at the ratio 0.5–0.9 ml sorbent/1 g cell biomass. The column was washed with two column volumes of Buffer A and a linear gradient of ten column volumes from 0.0 M to 0.3M of NaCl dissolved in Buffer A was applied with the flow speed 10 ml/cm$^2$ per hour. The enzyme eluted at 0.16–0.19M NaCl and was pooled. Pooled fractions were then dialyzed against 20–50 times higher volume of Buffer A supplemented with 100 mM NaCl overnight and loaded onto a Blue Sepharose (Amersham Pharmacia Biotech) column equilibrated with Buffer A supplemented with 100 mM NaCl at the ratio 0.3–0.8 ml sorbent/1 g cell biomass. The column was washed with two column volumes of Buffer A supplemented with 100 mM NaCl and a linear gradient of ten column volumes from 0.1M to 0.7M of NaCl dissolved in Buffer A was applied with the flow speed 10 ml/cm$^2$ per hour. The enzyme eluted at 0.48–0.65M NaCl and was pooled. Pooled fractions were then dialyzed against 20–50 times higher volume of Buffer A overnight and loaded onto a DEAE-52 Cellulose (Whatman) column equilibrated with Buffer A at the ratio 0.3–0.8 ml sorbent/1 g cell biomass. The column was washed with two column volumes of Buffer A and a linear gradient of ten column volumes from 0.0M to 0.3M of NaCl dissolved in Buffer A was applied with the flow speed 10 ml/cm$^2$ per hour. The enzyme eluted at 0.06–0.09M NaCl, was pooled and immediately loaded onto a Bordo Sepharose (MBI Fermentas) column equilibrated with Buffer A supplemented with 100 mM NaCl at the ratio 0.3–0.8 ml sorbent/1 g cell biomass. The column was washed with two column volumes of Buffer A supplemented with 100 mM NaCl and a linear gradient of ten column volumes from 0.1M to 0.8M of NaCl dissolved in Buffer A was applied with the flow speed 10 ml/cm$^2$ per hour. The enzyme eluted at 0.32–0.43M NaCl and was pooled. Pooled fractions were then dialyzed against 10–20 times higher volume of Storage Buffer (10 mM K$_2$HPO$_4$ pH 7.4, 100 mM NaCl, 1 mM EDTA, 7 mM β-mercaptoethanol, 50% v/v glycerol). The above purification scheme yielded apparently homogenous protein preparation with the molecular weight of about 108 kDa as confirmed by Coomasie blue R-250 stained SDS-PAGE gel electrophoresis. Protein concentration was measured according to Bradford and was found to be 0.7 mg/ml with specific activity 3.5 u/μg of protein when expressed in DNA methyltransferase units (determined as described in MBI Fermentas Catalogue).

Recognition specificity, cleavage mode and methylation specificity were determined for purified Eco57I mutant proteins.

Determination of the Recognition Specificity and Cleavage Site of Eco57I T862N Mutant Protein To determine the substrate specificity of the Eco57I T862N mutant variant it was incubated with 1 μg λ phage DNA for one hour at 37° C. in 50 μl of MBI Fermentas B+ buffer (10 mM Tris-HCl, pH 8.5, 100 mM KCl, 10 mM MgCl$_2$ and 0.1 mg/ml BSA) containing 0.01 mM SAM (FIG. 4). In parallel the same substrate was incubated with the following enzymes and enzyme mixtures: Eco57I (recognition sequence CTGAAG), GsuI (recognition sequence CTGGAG), Eco57I+GsuI, Eco57I+GsuI+Eco57I T862N. Electrophoretic analysis of restriction digests confirmed that the mutant variant cleaved DNA at both Eco57I and GsuI recognition sites, thereby its recognition sequence being 5' CTGPuAG3'.

pACYC 177 DNA was used as a template to characterize the cleavage position of Eco57I T862N mutant protein, namely the sites located at the positions 454 (GsuI) and 3798 (Eco57I). Four dideoxy sequencing reactions (G, A, T, C, respectively) using [α-33P]dATP were carried out. The same template and primers were used in the fifth non-terminating reaction, which also included T7 DNA polymerase, dNTPs and [α-33P]dATP. The extension reaction was heat inactivated, radiolabelled DNA was incubated with Eco57I T862N and, subsequently, the reaction mix was divided into two. One sample was treated with T4 DNA polymerase. Both samples were diluted with sequencing dye and loaded on a standard sequencing gel together with the dideoxy sequencing reactions. The cleavage site of Eco57I T862N was determined by comparison of dideoxy sequencing ladders with both the fragments generated by Eco57I T862N cleavage and DNA fragments obtained after the T4 DNA polymerase action on the digestion product.

Results of the determination Eco57I T862N cleavage site presented in FIG. 5 indicate that Eco57I T862N mutant protein cleaves DNA 16 and 14 nucleotides away from the site CTGGAG (GsuI) and 16 or 17 and 14 or 15 nucleotides away from the site CTGAAG (Eco57I), thereby exhibiting degenerate cleavage point for one of the sequences recognised.

The key to FIG. 5 is as follows:

Panel A: Reactions through GsuI recognition site.

Panel B: Reactions through Eco57I recognition site. G, A, T, C—sequencing ladders R—Extension products digested with Eco57I T862N T4—Extension products digested with Eco57I T862N after reaction with T4 DNA polymerase Panel C: Schematic representation of cleavage point determination of Eco57I T862N mutant protein:

Determination of the Methylation Specificity of Eco57I T862N and Eco57I D78K T862N Mutant Proteins The modification specificity was determined by using two oligodeoxyribonucleotide (30-mer and 36-mer) duplex DNA fragments containing the substrate sequence for the GsuI (#1) and Eco57I (#2) restriction endonucleases (presented in bold):

```
#1:                                    (SEQ ID NO:12)
        5'-AGTTCTGGAGCATCGTTCACCGGTTACAAC
                                       (SEQ ID NO:13)
           CTCTTCAAGACCTCGTAGGCAATGGCCAATGTTGGT-5'
#2:                                    (SEQ ID NO:14)
        5'-AGTTCTGAAGCATCGTTCACCGGTTACAAC
                                       (SEQ ID NO:15)
           CTCTTCAAGACTTCGTAGGCAATGGCCAATGTTGGT-5'
```

The methylation reaction was performed in 50 μl of B+ reaction buffer (MBI Fermentas) containing 100 pmol of the synthetic duplexes and 30 μM of [$^3$H-methyl]-AdoMet (67 Ci/mmol). 10 activity units as defined above of the Eco57I mutant proteins were added to relevant reaction mixtures and incubated for 3 h at 37° C. Reactions were stopped by adding 20 μl of sequencing dye, denatured by heating for 5 min. and loaded on 15% polyacrylamide gel under denaturing conditions.

To determine the capacity of Eco57I mutant proteins to modify different strands of the substrate, top and bottom strands of oligonucleotide duplex after PAGE were identified by ethidium bromide staining, excised from the gel and incorporated ³H-radioactivity was estimated by liquid scintillation counting. Results are presented in the table below:

| No | Oligonucleotide | H3-radioactivity | Enzyme |
|----|---|---|---|
| | Eco57I sequences | | |
| 1 | 5'-CTGAAG-3' | 21846 | Eco57I |
| | | | (MBI Fermentas) |
| 2 | 3'-GACTTC-5' | 406 | |
| 3 | 5'-CTGAAG-3' | 17886 | Eco57I T862N |
| 4 | 3'-GACTTC-5' | 198 | |
| 5 | 5'-CTGAAG-3' | 10170 | Eco57I D78K T862N |
| 6 | 3'-GACTTC-5' | 278 | |
| | GsuI sequences | | |
| 7 | 5'-CTGGAG-3' | 13206 | GsuI |
| | | | (MBI Fermentas) |
| 8 | 3'-GACCTC-5' | 664 | |
| 9 | 5'-CTGGAG-3' | 30574 | Eco57I T862N |
| 10 | 3'-GACCTC-5' | 980 | |
| 11 | 5'-CTGGAG-3' | 32151 | Eco57I D78K T862N |
| 12 | 3'-GACCTC-5' | 920 | |

Obtained data indicate, that mutant variants of Eco57I protein have altered methylation specificity: 5' CTGPuAG3', and, like Eco57I and GsuI restriction endonucleases, they methylate only one DNA strand.

GsuI is not the only one example of restriction enzymes that may be used for selection of Eco57I mutant variants according to disclosed method. For example, BglII, recognising DNA sequence AGATCT is sensitive to methylation produced by Eco57I when their sequence overlap: CTGAAGATCT (SEQ ID NO: 16) (Eco57I recognition sequence is underlined, modified base is bolded), therefore it may be used to select for the set of altered specificities of R.Eco57I listed below, provided that such sequences differing in at least one nucleotide from the one recognised by Eco57I and overlapping the recognition sequence for BglII are present in the cloning vehicle used for BglII digestion selection step (all sequences that would be recognised by newly created specificity of Eco57I mutant variants are underlined, methylated adenine is presented in bold and altered bases are in lower case):

| | |
|---|---|
| aTGAAGATCT | (SEQ ID NO:17) |
| tTGAAGATCT | (SEQ ID NO:18) |
| gTGAAGATCT | (SEQ ID NO:19) |
| CaGAAGATCT | (SEQ ID NO:20) |
| CcGAAGATCT | (SEQ ID NO:21) |
| CgGAAGATCT | (SEQ ID NO:22) |
| CTaAGATCT | (SEQ ID NO:23) |
| CTcAAGATCT | (SEQ ID NO:24) |
| CTtAAGATCT | (SEQ ID NO:25) |
| CTGtAGATCT | (SEQ ID NO:26) |
| CTGgAGATCT | (SEQ ID NO:27) |
| CTGcAGATCT | (SEQ ID NO:28) |

Likewise, HindIII restriction endonuclease, recognising sequence AAGCTT is sensitive to the methylation, produced by AloI restriction endonuclease (recognition sequence GGANNNNNNGTTC (SEQ ID NO: 5), methylated nucleotide in the top strand is presented in bold), when their recognition sequences overlap: GGAAGCTTNGTTC (SEQ ID NO: 29), therefore it may be used to select for the following set of altered specificities of AoII, provided that such sequences differing in at least one nucleotide from the one recognised by AoII and overlapping the recognition sequence for HindIII are present in the cloning vehicle used for HindIII digestion selection step (all sequences that would be recognised by newly created specificity of AoII mutant variants are underlined, methylated adenine is presented in bold):

| | |
|---|---|
| aGAAGCTTNGTTC | (SEQ ID NO:30) |
| tGAAGCTTNGTTC | (SEQ ID NO:31) |
| cGAAGCTTNGTTC | (SEQ ID NO:32) |
| GaAAGCTTNGTTC | (SEQ ID NO:33) |
| GtAAGCTTNGTTC | (SEQ ID NO:34) |
| GcAAGCTTNGTTC | (SEQ ID NO:35) |
| GGAAGCTTNaTTC | (SEQ ID NO:36) |
| GGAAGCTTNtTTC | (SEQ ID NO:37) |
| GGAAGCTTNcTTC | (SEQ ID NO:38) |
| GGAAGCTTNGaTC | (SEQ ID NO:39) |
| GGAAGCTTNGgTC | (SEQ ID NO:40) |
| GGAAGCTTNGcTC | (SEQ ID NO:41) |
| GGAAGCTTNGTaC | (SEQ ID NO:42) |
| GGAAGCTTNGTgC | (SEQ ID NO:43) |
| GGAAGCTTNGTcC | (SEQ ID NO:44) |
| GGAAGCTTNGTTa | (SEQ ID NO:45) |
| GGAAGCTTNGTTg | (SEQ ID NO:46) |
| GGAAGCTTNGTTt | (SEQ ID NO:47). |

The present method allows selection for mutant variants recognizing new sequences that differ not only in single nucleotide from that of the wild type enzyme but also for mutants that would recognize degenerate sequences or sequences differing in several nucleotides, especially if mutants of altered specificity are taken into the next round of mutagenesis and digestion-selection.

REFERENCES

1. Jeltsch, A. et al., Engineering novel restriction endonucleases: principles and applications, (1996), Trends in Biotechnology, vol. 14, No. 7, 235–238
2. Geiger, R. et al., Genetic engineering of EcoRI mutants with altered amino acid residues in the DNA binding site: physicochemical investigations give evidence for an altered monomer/dimer equilibrium for the Gln144Lys145 and Gln144Lys145Lys200 mutants, (1989), Biochemistry, vol. 28, No. 6, 2667–2677.
3. Alves, J. et al. Changing the hydrogen-bonding potential in the DNA binding site of EcoRI by site-directed mutagenesis drastically reduces the enzymatic activity, not, however, the preference of this restriction endonuclease for cleavage within the site-GAATTC, (1989), Biochemistry, vol. 28, No. 6, 2678–2684.

4. Hager, P. W., et al. Probing the role of glutamic acid 144 in the EcoRI endonuclease using aspartic acid and glutamine replacements, (1990), J. Biol. Chem., vol. 265, No. 35, 21520–21526.
5. Heitman J., Model, P. Mutants of the EcoRI endonuclease with promiscuous substrate specificity implicate residues involved in substrate recognition, (1990), EMBO J. vol. 9, No. 10, 3369–3378.
6. Osuna, J., et al Combinatorial mutagenesis of three major groove-contacting residues of EcoRI: single and double amino acid replacements retaining methyltransferase-sensitive activities, (1991), Gene, vol. 106, No. 1, 7–12.
7. Jeltsch, A., et al. Mutational analysis of the function of Gln115 in the EcoRI restriction endonuclease, a critical amino acid for recognition of the inner thymidine residue in the sequence -GAATTC- and for coupling specific DNA binding to catalysis, (1993), J Mol Biol., vol. 229, No. 1, 221–234.
8. Flores, H., et al. Saturation mutagenesis of His114 of EcoRI reveals relaxed-specificity mutants, (1995), Gene, vol. 157, No. 1–2, 295–301.
9. Thielking, V., et al. Site-directed mutagenesis studies with EcoRV restriction endonuclease to identify regions involved in recognition and catalysis, (1991), Biochemistry, vol. 30, No. 26, 6416–6422.
10. Wenz, C., et al. Protein engineering of the restriction endonuclease EcoRV: replacement of an amino acid residue in the DNA binding site leads to an altered selectivity towards unmodified and modified substrates, (1994), Biochim. Biophys. Acta, vol. 1219, No. 1, 73–80.
11. Lanio, T., et al. EcoRV-T94V: a mutant restriction endonuclease with an altered substrate specificity towards modified oligodeoxynucleotides, (1996), Protein Eng., vol. 9, No. 11, 1005–1010.
12. Dorner, L. F., et al. Genetic analysis of the base-specific contacts of BamHI restriction endonuclease, (1999), J. Mol. Biol., vol. 285, No. 4, 1515–1523.
13. Whitaker, R., et al. A mutant of BamHI restriction endonuclease which requires N6-methyladenine for cleavage, (1999), J. Mol. Biol., vol. 285, No. 4, 1525–1536.
14. Waugh, D., Sauer, R., A novel class of FokI restriction endonuclease mutants that cleave hemi-methy-lated substrates, (1994), J. Biol. Chem., vol. 269, No.16, 12298–12303
15. Schottler, S., et al. Protein engineering of the restriction endonuclease EcoRV—structure-guided design of enzyme variants that recognize the base pairs flanking the recognition site, (1998), Eur. J. Biochem., vol. 258, No. 1, 184–191
16. Lanio, T., et al. On the possibilities and limitations of rational protein design to expand the specificity of restriction enzymes: a case study employing EcoRV as the target, (2000), Protein Eng., vol. 13, No. 4, 275–281
17. Gubler, M., et al. Recombination of constant and variable modules alters DNA sequence recognition by type IC restriction-modification enzymes, (1992), EMBO J., vol. 11, No. 1, 233–240
18. Meister, J., et al. Macroevolution by transposition: drastic modification of DNA recognition by a type I restriction enzyme following Tn5 transposition, (1993), EMBO J., vol. 12, No. 12, 4585–4591
19. Kim, Y. G., Chandrasegaran, S., Chimeric restriction endonuclease, (1994), Proc. Natl. Acad. Sci. U S A, vol. 91, No. 3, 883–887
20. Kim, Y. G., Cha, J., Chandrasegaran, S., Hybrid restriction enzymes: zinc finger fusions to Fok I cleavage domain, (1996), Proc. Natl. Acad. Sci. U S A, vol. 93, No. 3, 1156–1160
21. Kim, Y. G., et al. Chimeric restriction enzyme: Gal4 fusion to FokI cleavage domain, (1998), Biol. Chem., vol. 379, No. 4–5, 489–495
22. Chandrasegaran, S., Smith, J., Chimeric restriction enzymes: what is next? (1999), Biol. Chem., vol. 380, No. 7–8, 841–848
23. Yanofsky, S. D., et al. Clustering of null mutations in the EcoRI endonuclease, (1987), Proteins, vol. 2, No. 4, 273–282
24. Vipond, I. B., Halford, S. E. Random mutagenesis targeted to the active site of the EcoRV restriction endonuclease, (1996), Biochemistry, vol. 35, No. 6, 1701–1711.
25. Janulaitis, A., et al. Purification and properties of the Eco57I restriction endonuclease and methylase—prototypes of a new class (type IV), (1992), Nucl. Acids Res., vol. 20, No. 22, 6043–6049
26. Janulaitis, A., et al. Cloning and sequence analysis of the genes coding for Eco57I typeIV restriction-modification enzymes, (1992), Nucl. Acids Res., vol. 20, No. 22, 6051–6056
27. Petrusyte, M. P., et al. New types of restriction endonucleases, (1987), Dokl. Akad. Nauk., No. 295, 1250–1253
28. Vaisvila, Cloning and analysis of type IV restriction-modification systems, PhD thesis, 1993
29. Kong, H., et al. Characterisation of BcgI, a new kind of restriction-modification system, (1994), J. Biol. Chem., vol. 269, No. 1, 683–690
30. Piekarowicz, A., et al. The HaeIV restriction-modification system of Haemophilus aegyptius is encoded by a single polypeptide, (1999), J. Mol. Biol., vol. 293, No. 5, 1055–1065
31. MBI Fermentas Molecular Biology Catalogue & Product Application Guide, 2000–2001, 26
32. Anderson, J. E. Restriction endonucleases and modification methylases, (1993), Curr. Opin. Struc. Biol., vol. 3, 24–30
33. Rimseliene, R., Timinskas, A., Site-directed mutagenesis of type IV restriction endonuclease Eco57I, (1997), Biologija, No.1, 31–33
34. Cesnaviciene, et al., unpublished
35. Leung, D. W., et al., A method for random mutagenesis of a defined DNA segment using a modified polymerase chain reaction, (1989), Techniques, vol.1, No. 1, 11–15
36. Zhou, Y., et al., Random mutagenesis of gene-sized molecules by use of PCR with Taq DNA polymerase, (1991), Nucl. Acids Res., vol. 19, No. 21, 6052
37. Stemmer, W. P., DNA shuffling by random fragmentation and reassembly: in vitro recombination for molecular evolution, (1994), Proc Natl Acad Sci USA, vol. 91, No. 22, 10747–10751
38. Stemmer, W. P., Rapid evolution of a protein in vitro by DNA shuffling. (1994), Nature, vol. 370, No. 6488, 389–391
39. Timinskas A, Butkus V, Janulaitis A. Sequence motifs characteristic for DNA [cytosine-N4] and DNA [adenine-N6] methyltranserases. Classification of all DNA methyltransferases. Gene. 1995 May 19;157(1–2):3–11
40. Malone T, Blumenthal R M, Cheng X. Structure-guided analysis reveals nine sequence motifs conserved among DNA amino-methyltransferases, and suggests a catalytic mechanism for these enzymes. J Mol Biol. 1995 Nov. 3;253(4):618–32
41. Kumar S, Cheng X, Klimasauskas S, Mi S, Posfai J, Roberts R J, Wilson G G. The DNA (cytosine-5) methyltransferases. Nucleic Acids Res. 1994 Jan. 11;22(1): 1–10

What is claimed is:

1. A process for producing a polynucleotide encoding a restriction endonuclease with an altered specificity, which process comprises:

(a) mutagenising a polynucleotide encoding a restriction endonuclease with specificity for a recognition sequence so as to produce one or more mutated polynucleotides; and (b) isolating therefrom a polynucleotide encoding a mutated restriction endonuclease with specificity for an altered recognition sequence by selecting a polynucleotide which expresses a restriction endonuclease with methylase specificity for the altered recognition sequence.

2. A process for producing a polynucleotide encoding a restriction endonuclease with an altered specificity, which process comprises:

(a) mutagenising a polynucleotide encoding a restriction endonuclease with specificity for a recognition sequence so as to produce one or more mutated polynucleotides, which restriction endonuclease has methylase activity towards a target base in the recognition sequence; and (b) isolating therefrom a polynucleotide encoding a mutated restriction endonuclease with specificity for an altered recognition sequence by selecting a polynucleotide which expresses a restriction endonuclease with methylase specificity for the altered recognition sequence, wherein the altered recognition sequence comprises the recognition sequence altered in at least one nucleotide base.

3. A process according to claim 2, wherein the restriction endonuclease comprises a type I restriction endonuclease, a type II restriction endonuclease containing in its amino acid sequence a motif characteristic of a DNA methyltransferase, a type III restriction endonuclease or a type IV restriction endonuclease.

4. A process according to claim 3, wherein the restriction endonuclease comprises Eco57I.

5. A process according to claim 3, wherein the restriction endonuclease comprises BcgI, HaeIV or AloI.

6. A process for producing a polynucleotide encoding a restriction endonuclease with an altered specificity, which process comprises:
   (a) mutagenising a polynucleotide encoding a restriction endonuclease so as to produce a polynucleotide library comprising mutated polynucleotides, which restriction endonuclease has specificity for a recognition sequence and methylase activity towards a target base in the recognition sequence;
   (b) incorporating each mutated polynucleotide into a polynucleotide vector to form a vector library, wherein the polynucleotide vector has a sub-sequence comprising an altered sequence which comprises the recognition sequence altered in at least one nucleotide base, and a selection sequence overlapping the altered sequence to an extent which includes the target base;
   (c) propagating the vector library to form a propagated library under conditions to permit restriction endonuclease catalysed polynucleotide methylase activity;
   (d) treating the propagated library with a selection restriction endonuclease with specificity for the selection sequence and sensitivity to methylation in the selection sequence to cleave polynucleotides containing unmethylated selection sequences; and
   (e) isolating therefrom an uncleaved polynucleotide encoding a restriction endonuclease with specificity for the altered sequence.

7. A process according to claim 6, wherein the selection restriction endonuclease comprises GsuI or BglII when the restriction endonuclease comprises Eco57I.

8. A process according to claim 6, wherein the selection restriction endonuclease comprises HindIII when the restriction endonuclease comprises AloI.

9. A process according to claim 6, wherein the step of propagating the vector library comprises transforming a host cell therewith and propagating the host cells.

10. A process according to claim 9, which further comprises isolating the propagated library from the host cells following their propagation.

11. A process according to claim 1, wherein the polynucleotide mutagenised in step (a) of claim 1 encodes a restriction endonuclease prepared by (i) selecting a methylase-deficient restriction endonuclease which has in its amino acid sequence a motif characteristic of a DNA methyltransferase; and (ii) restoring methylase activity in the methylase deficient restriction endonuclease.

12. A process according to claim 11, wherein the step of restoring methylase activity comprises:

(a) mutagenising a polynucleotide encoding the methylase-deficient restriction endonuclease so as to produce a polynucleotide library comprising mutated polynucleotides, which restriction endonuclease has specificity for a recognition sequence;
   (b) incorporating each mutated polynucleotide into a polynucleotide vector to form a vector library, which polynucleotide vector has the recognition sequence;
   (c) propagating the vector library to form a propagated library under conditions to permit restriction endonuclease catalysed polynucleotide methylase activity;
   (d) treating the propagated library with a restriction endonuclease with specificity for the recognition sequence to cleave polynucleotides containing an unmethylated recognition sequence; and
   (e) isolating therefrom an uncleaved polynucleotide encoding a restriction endonuclease with methylase activity.

13. A process for producing a restriction endonuclease with an altered specificity, which comprises producing a polynucleotide encoding a restriction endonuclease in accordance with claim 1, expressing the restriction endonuclease and harvesting the restriction endonuclease.

14. A polynucleotide encoding a restriction endonuclease with altered specificity, obtained by a process according to claim 1.

15. A polynucleotide which encodes a restriction endonuclease which comprises an Eco57I or mutant or variant thereof with specificity for a recognition sequence comprising 5'-CTGRAG-3'.

16. A restriction endonuclease obtainable from a process according to claim 13.

17. A restriction endonuclease which comprises an Eco57I or mutant or variant thereof with specificity for a recognition sequence comprising 5'-CTGRAG-3'.

18. A process for producing a restriction endonuclease with an altered specificity, which comprises producing a polynucleotide encoding a restriction endonuclease in accordance with claim 2, expressing the restriction endonuclease and harvesting the restriction endonuclease.

19. A process for producing a restriction endonuclease with an altered specificity, which comprises producing a polynucleotide encoding a restriction endonuclease in accordance with claim 6, expressing the restriction endonuclease and harvesting the restriction endonuclease.

20. A polynucleotide encoding a restriction endonuclease with altered specificity, obtained by a process according to claim 2.

21. A polynucleotide encoding a restriction endonuclease with altered specificity, obtained by a process according to claim 6.

* * * * *

SEQUENCE LISTING

<160> NUMBER OF SEQ ID NOS: 51

<210> SEQ ID NO 1
<211> LENGTH: 13
<212> TYPE: DNA
<213> ORGANISM: Artificial Sequence
<220> FEATURE:
<223> OTHER INFORMATION: Restriction endonuclease recognition sequence
<220> FEATURE:
<221> NAME/KEY: misc_binding
<222> LOCATION: (1)..(13)
<223> OTHER INFORMATION: Recognition sequence for StyR124I
<220> FEATURE:
<221> NAME/KEY: misc_feature
<222> LOCATION: (4)..(9)
<223> OTHER INFORMATION: n is A, C, G or T

<400> SEQUENCE: 1
gaannnnnnr tcg                                                    13

<210> SEQ ID NO 2
<211> LENGTH: 14
<212> TYPE: DNA
<213> ORGANISM: Artificial Sequence
<220> FEATURE:
<223> OTHER INFORMATION: Restriction endonuclease recognition sequence
<220> FEATURE:
<221> NAME/KEY: misc_binding
<222> LOCATION: (1)..(14)
<223> OTHER INFORMATION: Recognition sequence of EcoDXXI
<220> FEATURE:
<221> NAME/KEY: misc_feature
<222> LOCATION: (4)..(10)
<223> OTHER INFORMATION: n is A, C G or T

<400> SEQUENCE: 2
tcannnnnnn rttc                                                   14

<210> SEQ ID NO 3
<211> LENGTH: 13
<212> TYPE: DNA
<213> ORGANISM: Artificial Sequence
<220> FEATURE:
<223> OTHER INFORMATION: Restriction endonuclease recognition sequence
<220> FEATURE:
<221> NAME/KEY: misc_binding
<222> LOCATION: (1)..(13)
<223> OTHER INFORMATION: Recognition sequence of hybrid endonuclease
      obtained by fusing the N-terminal half of hsdS subunit from
      StyR124I with the C-terminal half of the hsdS subunit from EcoDXXI
<220> FEATURE:
<221> NAME/KEY: misc_feature
<222> LOCATION: (4)..(9)
<223> OTHER INFORMATION: n is A, C, G or T

<400> SEQUENCE: 3
gaannnnnnr ttc                                                    13

<210> SEQ ID NO 4
<211> LENGTH: 14
<212> TYPE: DNA
<213> ORGANISM: Artificial Sequence
<220> FEATURE:
<223> OTHER INFORMATION: Restriction endonuclease recognition sequence
<220> FEATURE:
<221> NAME/KEY: misc_binding
<222> LOCATION: (1)..(14)
<223> OTHER INFORMATION: Recognition sequence of mutant generated by
      insertion of Tn5 transposon into the hsdS subunit of EcoDXXI
<220> FEATURE:

<221> NAME/KEY: misc_feature
<222> LOCATION: (4)..(11)
<223> OTHER INFORMATION: n is A, C, G or T

<400> SEQUENCE: 4
tcannnnnnn ntga                                                    14

<210> SEQ ID NO 5
<211> LENGTH: 13
<212> TYPE: DNA
<213> ORGANISM: Artificial Sequence
<220> FEATURE:
<223> OTHER INFORMATION: Restriction endonuclease recognition sequence
<220> FEATURE:
<221> NAME/KEY: misc_binding
<222> LOCATION: (1)..(13)
<223> OTHER INFORMATION: Recognition sequence of AloI
<220> FEATURE:
<221> NAME/KEY: misc_feature
<222> LOCATION: (4)..(9)
<223> OTHER INFORMATION: n is A, C, G or T

<400> SEQUENCE: 5
ggannnnnng ttc                                                     13

<210> SEQ ID NO 6
<211> LENGTH: 22
<212> TYPE: DNA
<213> ORGANISM: Artificial Sequence
<220> FEATURE:
<223> OTHER INFORMATION: Restriction endonuclease recognition sequence
<220> FEATURE:
<221> NAME/KEY: misc_binding
<222> LOCATION: (1)..(22)
<223> OTHER INFORMATION: Recognition sequence of Eco57I
<220> FEATURE:
<221> NAME/KEY: misc_feature
<222> LOCATION: (7)..(22)
<223> OTHER INFORMATION: n is A, C, G or T

<400> SEQUENCE: 6
ctgaagnnnn nnnnnnnnnn nn                                           22

<210> SEQ ID NO 7
<211> LENGTH: 18
<212> TYPE: PRT
<213> ORGANISM: Artificial Sequence
<220> FEATURE:
<223> OTHER INFORMATION: Amino acid motif
<220> FEATURE:
<221> NAME/KEY: REPEAT
<222> LOCATION: (1)..(18)
<223> OTHER INFORMATION: Amino acid motif present in Eco57I
<220> FEATURE:
<221> NAME/KEY: misc_feature
<222> LOCATION: (3)..(15)
<223> OTHER INFORMATION: Xaa is any amino acid
<220> FEATURE:
<221> NAME/KEY: misc_feature
<222> LOCATION: (17)..(17)
<223> OTHER INFORMATION: Xaa is any amio acid

<400> SEQUENCE: 7

Pro Asp Xaa Xaa Xaa Xaa Xaa Xaa Xaa Xaa Xaa Xaa Xaa Xaa Xaa Glu
1               5                   10                  15
Xaa Lys

<210> SEQ ID NO 8
<211> LENGTH: 25
<212> TYPE: PRT
<213> ORGANISM: Artificial Sequence

```
<220> FEATURE:
<223> OTHER INFORMATION: Amino acid motif
<220> FEATURE:
<221> NAME/KEY: PEPTIDE
<222> LOCATION: (1)..(25)
<223> OTHER INFORMATION: Amino acid motif present in Eco57I
<220> FEATURE:
<221> NAME/KEY: misc_feature
<222> LOCATION: (3)..(22)
<223> OTHER INFORMATION: Xaa is any amino acid
<220> FEATURE:
<221> NAME/KEY: misc_feature
<222> LOCATION: (24)..(24)
<223> OTHER INFORMATION: Xaa is any amino acid

<400> SEQUENCE: 8

Pro Asp Xaa Xaa Xaa Xaa Xaa Xaa Xaa Xaa Xaa Xaa Xaa Xaa Xaa
1               5                   10                  15

Xaa Xaa Xaa Xaa Xaa Xaa Asp Xaa Lys
            20                  25

<210> SEQ ID NO 9
<211> LENGTH: 22
<212> TYPE: DNA
<213> ORGANISM: Artificial Sequence
<220> FEATURE:
<223> OTHER INFORMATION: Restriction endonuclease recognition sequence
<220> FEATURE:
<221> NAME/KEY: misc_binding
<222> LOCATION: (1)..(22)
<223> OTHER INFORMATION: Recognition sequence of GsuI
<220> FEATURE:
<221> NAME/KEY: misc_feature
<222> LOCATION: (7)..(22)
<223> OTHER INFORMATION: n is A, C, G or T

<400> SEQUENCE: 9
ctggagnnnn nnnnnnnnnn nn                                        22

<210> SEQ ID NO 10
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(30)
<223> OTHER INFORMATION: Primer complementary to 1495-1524 of eco57IR
      gene

<400> SEQUENCE: 10
gcttgataga tagtggagac aaagttaaac                                 30

<210> SEQ ID NO 11
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(23)
<223> OTHER INFORMATION: Primer complementary to 3065-3087 of eco75IR
      gene

<400> SEQUENCE: 11
gtaagtaggg atccaaaagt cgg                                        23

<210> SEQ ID NO 12
```

```
<211> LENGTH: 30
<212> TYPE: DNA
<213> ORGANISM: Artificial Sequence
<220> FEATURE:
<223> OTHER INFORMATION: Oligodeoxyribonucleotide containing GsuI
      recognition site
<220> FEATURE:
<221> NAME/KEY: protein_bind
<222> LOCATION: (1)..(30)
<223> OTHER INFORMATION: Watson strand of oligonucleotide probe
      containing GsuI binding site

<400> SEQUENCE: 12
agttctggag catcgttcac cggttacaac                                          30

<210> SEQ ID NO 13
<211> LENGTH: 36
<212> TYPE: DNA
<213> ORGANISM: Artificial Sequence
<220> FEATURE:
<223> OTHER INFORMATION: Oligodeoxyribonucleotide probe containing GsuI
      recognition site
<220> FEATURE:
<221> NAME/KEY: protein_bind
<222> LOCATION: (1)..(36)
<223> OTHER INFORMATION: 5'-3' sequence of Crick strand of
      oligonucleotide probe containing GsuI recognition sequence

<400> SEQUENCE: 13
tggttgtaac cggtaacgga tgctccagaa cttctc                                   36

<210> SEQ ID NO 14
<211> LENGTH: 30
<212> TYPE: DNA
<213> ORGANISM: Artificial Sequence
<220> FEATURE:
<223> OTHER INFORMATION: Oligodeoxyribonucleotide probe containing
      Eco75I recognition sequence
<220> FEATURE:
<221> NAME/KEY: protein_bind
<222> LOCATION: (1)..(30)
<223> OTHER INFORMATION: Watson strand of oligonucleotide probe
      containing Eco57I recognition sequence

<400> SEQUENCE: 14
agttctgaag catcgttcac cggttacaac                                          30

<210> SEQ ID NO 15
<211> LENGTH: 36
<212> TYPE: DNA
<213> ORGANISM: Artificial Sequence
<220> FEATURE:
<223> OTHER INFORMATION: Oligodeoxyribonucleotide probe containing
      Eco57I recognition sequence
<220> FEATURE:
<221> NAME/KEY: protein_bind
<222> LOCATION: (1)..(36)
<223> OTHER INFORMATION: 5'-3' sequence of Crick strand of
      oligonucleotide probe containing Eco57I recognition sequence

<400> SEQUENCE: 15
tggttgtaac cggtaacgga tgcttcagaa cttctc                                   36

<210> SEQ ID NO 16
<211> LENGTH: 10
<212> TYPE: DNA
<213> ORGANISM: Artificial Sequence
<220> FEATURE:
<223> OTHER INFORMATION: Oligonucleotide containing BglII and Eco57I
      recognition sequences
<220> FEATURE:
```

```
<221> NAME/KEY: protein_bind
<222> LOCATION: (1)..(10)
<223> OTHER INFORMATION: Oligonucleotide containing recognition
      sequences for BglII and Eco57I

<400> SEQUENCE: 16
ctgaagatct                                                                10

<210> SEQ ID NO 17
<211> LENGTH: 10
<212> TYPE: DNA
<213> ORGANISM: Artificial Sequence
<220> FEATURE:
<223> OTHER INFORMATION: Oligonucleotide containing mutated Eco57I
      recognition sequence and BglII recognition sequence
<220> FEATURE:
<221> NAME/KEY: protein_bind
<222> LOCATION: (1)..(10)
<223> OTHER INFORMATION: Oligonucleotide containing mutated Eco57I
      recognition sequence and BglII recognition sequence

<400> SEQUENCE: 17
atgaagatct                                                                10

<210> SEQ ID NO 18
<211> LENGTH: 10
<212> TYPE: DNA
<213> ORGANISM: Artificial Sequence
<220> FEATURE:
<223> OTHER INFORMATION: Oligonucleotide containing mutated Eco57I
      recognition sequence and BglII recognition sequence
<220> FEATURE:
<221> NAME/KEY: protein_bind
<222> LOCATION: (1)..(10)
<223> OTHER INFORMATION: Oligonucleotide containing mutated Eco57I
      recognition sequence and BglII recognition sequence

<400> SEQUENCE: 18
ttgaagatct                                                                10

<210> SEQ ID NO 19
<211> LENGTH: 10
<212> TYPE: DNA
<213> ORGANISM: Artificial Sequence
<220> FEATURE:
<223> OTHER INFORMATION: Oligonucleotide containing mutated Eco57I
      recognition sequence and BglII recognition sequence
<220> FEATURE:
<221> NAME/KEY: protein_bind
<222> LOCATION: (1)..(10)
<223> OTHER INFORMATION: Oligonucleotide containing mutated Eco57I
      recognition sequence and BglII recognition sequence

<400> SEQUENCE: 19
gtgaagatct                                                                10

<210> SEQ ID NO 20
<211> LENGTH: 10
<212> TYPE: DNA
<213> ORGANISM: Artificial Sequence
<220> FEATURE:
<223> OTHER INFORMATION: Oligonucleotide containing mutated Eco57I
      recognition sequence and BglII recognition sequence
<220> FEATURE:
<221> NAME/KEY: protein_bind
<222> LOCATION: (1)..(10)
<223> OTHER INFORMATION: Oligonucleotide containing mutated Eco57I
      recognition sequence and BglII recognition sequence

<400> SEQUENCE: 20
```
cagaagatct                                                          10

<210> SEQ ID NO 21
<211> LENGTH: 10
<212> TYPE: DNA
<213> ORGANISM: Artificial Sequence
<220> FEATURE:
<223> OTHER INFORMATION: Oligonucleotide containing mutated Eco57I
      recognition sequence and BglII recognition sequence
<220> FEATURE:
<221> NAME/KEY: protein_bind
<222> LOCATION: (1)..(10)
<223> OTHER INFORMATION: Oligonucleotide containing mutated Eco57I
      recognition sequence and BglII recognition sequence

<400> SEQUENCE: 21
ccgaagatct                                                          10

<210> SEQ ID NO 22
<211> LENGTH: 10
<212> TYPE: DNA
<213> ORGANISM: Artificial Sequence
<220> FEATURE:
<223> OTHER INFORMATION: Oligonucleotide containing mutated Eco57I
      recognition sequence and BglII recognition sequence
<220> FEATURE:
<221> NAME/KEY: protein_bind
<222> LOCATION: (1)..(10)
<223> OTHER INFORMATION: Oligonucleotide containing mutated Eco57I
      recognition sequence and BglII recognition sequence

<400> SEQUENCE: 22
cggaagatct                                                          10

<210> SEQ ID NO 23
<211> LENGTH: 10
<212> TYPE: DNA
<213> ORGANISM: Artificial Sequence
<220> FEATURE:
<223> OTHER INFORMATION: Oligonucleotide containing mutated Eco57I
      recognition sequence and BglII recognition sequence
<220> FEATURE:
<221> NAME/KEY: protein_bind
<222> LOCATION: (1)..(10)
<223> OTHER INFORMATION: Oligonucleotide containing mutated Eco57I
      recognition sequence and BglII recognition sequence

<400> SEQUENCE: 23
ctaaagatct                                                          10

<210> SEQ ID NO 24
<211> LENGTH: 10
<212> TYPE: DNA
<213> ORGANISM: Artificial Sequence
<220> FEATURE:
<223> OTHER INFORMATION: Oligonucleotide containing mutated Eco57I
      recognition sequence and BglII recognition sequence
<220> FEATURE:
<221> NAME/KEY: protein_bind
<222> LOCATION: (1)..(10)
<223> OTHER INFORMATION: Oligonucleotide containing mutated Eco57I
      recogntion sequence and BglII recognition sequence

<400> SEQUENCE: 24
ctcaagatct                                                          10

<210> SEQ ID NO 25
<211> LENGTH: 10
<212> TYPE: DNA
<213> ORGANISM: Artificial Sequence

```
<220> FEATURE:
<223> OTHER INFORMATION: Oligonucleotide containing mutated Eco57I
      recognition sequence and BglII recognition sequence
<220> FEATURE:
<221> NAME/KEY: protein_bind
<222> LOCATION: (1)..(10)
<223> OTHER INFORMATION: Oligonucleotide containing mutated Eco57I
      recognition sequence and BglII recognition sequence

<400> SEQUENCE: 25
cttaagatct                                                         10

<210> SEQ ID NO 26
<211> LENGTH: 10
<212> TYPE: DNA
<213> ORGANISM: Artificial Sequence
<220> FEATURE:
<223> OTHER INFORMATION: Oligonucleotide containing mutated Eco57I
      recogntion sequence and BglII recognition sequence
<220> FEATURE:
<221> NAME/KEY: protein_bind
<222> LOCATION: (1)..(10)
<223> OTHER INFORMATION: Oligonucleotide containing mutated Eco57I
      recognition sequence and BglII recognition sequence

<400> SEQUENCE: 26
ctgtagatct                                                         10

<210> SEQ ID NO 27
<211> LENGTH: 10
<212> TYPE: DNA
<213> ORGANISM: Artificial Sequence
<220> FEATURE:
<223> OTHER INFORMATION: Oligonucleotide containing mutated Eco57I
      recognition sequence and BglII recognition sequence
<220> FEATURE:
<221> NAME/KEY: protein_bind
<222> LOCATION: (1)..(10)
<223> OTHER INFORMATION: Oligonucleotide containing mutated Eco57I
      recognition sequence and BglII recognition sequence

<400> SEQUENCE: 27
ctggagatct                                                         10

<210> SEQ ID NO 28
<211> LENGTH: 10
<212> TYPE: DNA
<213> ORGANISM: Artificial Sequence
<220> FEATURE:
<223> OTHER INFORMATION: Oligonucleotide containing mutated Eco57I
      recognition sequence and BglII recognition sequence
<220> FEATURE:
<221> NAME/KEY: protein_bind
<222> LOCATION: (1)..(10)
<223> OTHER INFORMATION: Oligonucleotide containing mutated Eco57I
      recognition sequence and BglII recognition sequence

<400> SEQUENCE: 28
ctgcagatct                                                         10

<210> SEQ ID NO 29
<211> LENGTH: 13
<212> TYPE: DNA
<213> ORGANISM: Artificial Sequence
<220> FEATURE:
<223> OTHER INFORMATION: Oligonucleotide containing HindIII recognition
      sequence and AloI recognition sequence
<220> FEATURE:
<221> NAME/KEY: protein_bind
<222> LOCATION: (1)..(13)
<223> OTHER INFORMATION: Oligonucleotide containing HindIII recognition
```

```
           sequence and AloI recognition sequence
<220> FEATURE:
<221> NAME/KEY: misc_feature
<222> LOCATION: (9)..(9)
<223> OTHER INFORMATION: n is A, C, G or T

<400> SEQUENCE: 29
ggaagcttng ttc                                                          13

<210> SEQ ID NO 30
<211> LENGTH: 13
<212> TYPE: DNA
<213> ORGANISM: Artificial Sequence
<220> FEATURE:
<223> OTHER INFORMATION: Oligonucleotide containing mutated AloI
      recognition sequence and HindIII recognition sequence
<220> FEATURE:
<221> NAME/KEY: protein_bind
<222> LOCATION: (1)..(13)
<223> OTHER INFORMATION: Oligonucleotide containing mutated AloI
      recognition sequence and HindIII recognition sequence
<220> FEATURE:
<221> NAME/KEY: misc_feature
<222> LOCATION: (9)..(9)
<223> OTHER INFORMATION: n is A, C, G or T

<400> SEQUENCE: 30
agaagcttng ttc                                                          13

<210> SEQ ID NO 31
<211> LENGTH: 13
<212> TYPE: DNA
<213> ORGANISM: Artificial Sequence
<220> FEATURE:
<223> OTHER INFORMATION: Oligonucleotide containing mutated AloI
      recognition sequence and HindIII recognition sequence
<220> FEATURE:
<221> NAME/KEY: misc_feature
<222> LOCATION: (9)..(9)
<223> OTHER INFORMATION: n is A, C, G or T

<400> SEQUENCE: 31
tgaagcttng ttc                                                          13

<210> SEQ ID NO 32
<211> LENGTH: 13
<212> TYPE: DNA
<213> ORGANISM: Artificial Sequence
<220> FEATURE:
<223> OTHER INFORMATION: Oligonucleotide containing mutated AloI
      recognition sequence and HindIII recognition sequence
<220> FEATURE:
<221> NAME/KEY: protein_bind
<222> LOCATION: (1)..(13)
<223> OTHER INFORMATION: Oligonucleotide containing mutated AloI
      recognition sequence and HindIII recognition sequence
<220> FEATURE:
<221> NAME/KEY: misc_feature
<222> LOCATION: (9)..(9)
<223> OTHER INFORMATION: n is A, C, G or T

<400> SEQUENCE: 32
cgaagcttng ttc                                                          13

<210> SEQ ID NO 33
<211> LENGTH: 13
<212> TYPE: DNA
<213> ORGANISM: Artificial Sequence
<220> FEATURE:
<223> OTHER INFORMATION: Oligonucleotide containing mutated AloI
      recognition sequence and HindIII recognition sequence
```

```
<220> FEATURE:
<221> NAME/KEY: protein_bind
<222> LOCATION: (1)..(13)
<223> OTHER INFORMATION: Oligonucleotide containing mutated AloI
      recognition sequence and HindIII recognition sequence
<220> FEATURE:
<221> NAME/KEY: misc_feature
<222> LOCATION: (9)..(9)
<223> OTHER INFORMATION: n is A, C, G or T

<400> SEQUENCE: 33
gaaagcttng ttc                                                        13

<210> SEQ ID NO 34
<211> LENGTH: 13
<212> TYPE: DNA
<213> ORGANISM: Artificial Sequence
<220> FEATURE:
<223> OTHER INFORMATION: Oligonucleotide containing mutated AloI
      recognition sequence and HindIII recognition sequence
<220> FEATURE:
<221> NAME/KEY: protein_bind
<222> LOCATION: (1)..(13)
<223> OTHER INFORMATION: Oligonucleotide containing mutated AloI
      recognition sequence and HindIII recognition sequence
<220> FEATURE:
<221> NAME/KEY: misc_feature
<222> LOCATION: (9)..(9)
<223> OTHER INFORMATION: n is A, C, G or T

<400> SEQUENCE: 34
gtaagcttng ttc                                                        13

<210> SEQ ID NO 35
<211> LENGTH: 13
<212> TYPE: DNA
<213> ORGANISM: Artificial Sequence
<220> FEATURE:
<223> OTHER INFORMATION: Oligonucleotide containing mutated AloI
      recognition sequence and HindIII recognition sequence
<220> FEATURE:
<221> NAME/KEY: protein_bind
<222> LOCATION: (1)..(13)
<223> OTHER INFORMATION: Oligonucleotide containing mutated AloI
      recognition sequence and HindIII recognition sequence
<220> FEATURE:
<221> NAME/KEY: misc_feature
<222> LOCATION: (9)..(9)
<223> OTHER INFORMATION: n is A, C, G or T

<400> SEQUENCE: 35
gcaagcttng ttc                                                        13

<210> SEQ ID NO 36
<211> LENGTH: 13
<212> TYPE: DNA
<213> ORGANISM: Artificial Sequence
<220> FEATURE:
<223> OTHER INFORMATION: Oligonucleotide containing mutated AloI
      recognition sequence and HindIII recognition sequence
<220> FEATURE:
<221> NAME/KEY: protein_bind
<222> LOCATION: (1)..(13)
<223> OTHER INFORMATION: Oligonucleotide containing mutated AloI
      recognition sequence and HindIII recognition sequence
<220> FEATURE:
<221> NAME/KEY: misc_feature
<222> LOCATION: (9)..(9)
<223> OTHER INFORMATION: n is A, C, G or T

<400> SEQUENCE: 36
ggaagcttna ttc                                                        13
```

<210> SEQ ID NO 37
<211> LENGTH: 13
<212> TYPE: DNA
<213> ORGANISM: Artificial Sequence
<220> FEATURE:
<223> OTHER INFORMATION: Oligonucleotide containing mutated AloI
      recognition sequence and HindIII recognition sequence
<220> FEATURE:
<221> NAME/KEY: protein_bind
<222> LOCATION: (1)..(13)
<223> OTHER INFORMATION: Oligonucleotide containing mutated AloI
      recognition sequence and HindIII recognition sequence
<220> FEATURE:
<221> NAME/KEY: misc_feature
<222> LOCATION: (9)..(9)
<223> OTHER INFORMATION: n is A, C, G or T

<400> SEQUENCE: 37
ggaagcttnt ttc                                                          13

<210> SEQ ID NO 38
<211> LENGTH: 13
<212> TYPE: DNA
<213> ORGANISM: Artificial Sequence
<220> FEATURE:
<223> OTHER INFORMATION: Oligonucleotide containing mutated AloI
      recognition sequence and HindIII recognition sequence
<220> FEATURE:
<221> NAME/KEY: protein_bind
<222> LOCATION: (1)..(13)
<223> OTHER INFORMATION: Oligonucleotide containing mutated AloI
      recognition sequence and HindIII recognition sequence
<220> FEATURE:
<221> NAME/KEY: misc_feature
<222> LOCATION: (9)..(9)
<223> OTHER INFORMATION: n is A, C, G or T

<400> SEQUENCE: 38
ggaagcttnc ttc                                                          13

<210> SEQ ID NO 39
<211> LENGTH: 13
<212> TYPE: DNA
<213> ORGANISM: Artificial Sequence
<220> FEATURE:
<223> OTHER INFORMATION: Oligonucleotide containing mutated AloI
      recognition sequence and HindIII recognition sequence
<220> FEATURE:
<221> NAME/KEY: protein_bind
<222> LOCATION: (1)..(13)
<223> OTHER INFORMATION: Oligonucleotide containing mutated AloI
      recognition sequence and HindIII recognition sequence
<220> FEATURE:
<221> NAME/KEY: misc_feature
<222> LOCATION: (9)..(9)
<223> OTHER INFORMATION: n is A, C, G or T

<400> SEQUENCE: 39
ggaagcttng atc                                                          13

<210> SEQ ID NO 40
<211> LENGTH: 13
<212> TYPE: DNA
<213> ORGANISM: Artificial Sequence
<220> FEATURE:
<223> OTHER INFORMATION: Oligonucleotide containing mutated AloI
      recognition sequence and HindIII recognition sequence
<220> FEATURE:
<221> NAME/KEY: protein_bind
<222> LOCATION: (1)..(13)
<223> OTHER INFORMATION: Oligonucleotide containing mutated AloI

```
        recognition sequence and HindIII recognition sequence
<220> FEATURE:
<221> NAME/KEY: misc_feature
<222> LOCATION: (9)..(9)
<223> OTHER INFORMATION: n is A, C, G or T

<400> SEQUENCE: 40
ggaagcttng gtc                                                          13

<210> SEQ ID NO 41
<211> LENGTH: 13
<212> TYPE: DNA
<213> ORGANISM: Artificial Sequence
<220> FEATURE:
<223> OTHER INFORMATION: Oligonucleotide containing mutated AloI
        recognition sequence and HindIII recognition sequence
<220> FEATURE:
<221> NAME/KEY: protein_bind
<222> LOCATION: (1)..(13)
<223> OTHER INFORMATION: Oligonucleotide containing mutated AloI
        recognition sequence and HindIII recognition sequence
<220> FEATURE:
<221> NAME/KEY: misc_feature
<222> LOCATION: (9)..(9)
<223> OTHER INFORMATION: n is A, C, G or T

<400> SEQUENCE: 41
ggaagcttng ctc                                                          13

<210> SEQ ID NO 42
<211> LENGTH: 13
<212> TYPE: DNA
<213> ORGANISM: Artificial Sequence
<220> FEATURE:
<223> OTHER INFORMATION: Oligonucleotide containing mutated AloI
        recognition sequence and HindIII recognition sequence
<220> FEATURE:
<221> NAME/KEY: protein_bind
<222> LOCATION: (1)..(13)
<223> OTHER INFORMATION: Oligonucleotide containing mutated AloI
        recognition sequence and HindIII recognition sequence
<220> FEATURE:
<221> NAME/KEY: misc_feature
<222> LOCATION: (9)..(9)
<223> OTHER INFORMATION: n is A, C, G or T

<400> SEQUENCE: 42
ggaagcttng tac                                                          13

<210> SEQ ID NO 43
<211> LENGTH: 13
<212> TYPE: DNA
<213> ORGANISM: Artificial Sequence
<220> FEATURE:
<223> OTHER INFORMATION: Oligonucleotide containing mutated AloI
        recognition sequence and HindIII recognition sequence
<220> FEATURE:
<221> NAME/KEY: protein_bind
<222> LOCATION: (1)..(13)
<223> OTHER INFORMATION: Oligonucleotide containing mutated AloI
        recognition sequence and HindIII recognition sequence
<220> FEATURE:
<221> NAME/KEY: misc_feature
<222> LOCATION: (9)..(9)
<223> OTHER INFORMATION: n is A, C, G or T

<400> SEQUENCE: 43
ggaagcttng tgc                                                          13

<210> SEQ ID NO 44
<211> LENGTH: 13
```

```
<212> TYPE: DNA
<213> ORGANISM: Artificial Sequence
<220> FEATURE:
<223> OTHER INFORMATION: Oligonucleotide containing mutated AloI
      recognition sequence and HindIII recognition sequence
<220> FEATURE:
<221> NAME/KEY: protein_bind
<222> LOCATION: (1)..(13)
<223> OTHER INFORMATION: Oligonucleotide containing mutated AloI
      recognition sequence and HindIII recognition sequence
<220> FEATURE:
<221> NAME/KEY: misc_feature
<222> LOCATION: (9)..(9)
<223> OTHER INFORMATION: n is A, C, G or T

<400> SEQUENCE: 44
ggaagcttng tcc                                                      13

<210> SEQ ID NO 45
<211> LENGTH: 13
<212> TYPE: DNA
<213> ORGANISM: Artificial Sequence
<220> FEATURE:
<223> OTHER INFORMATION: Oligonucleotide containing mutated AloI
      recognition sequence and HindIII recognition sequence
<220> FEATURE:
<221> NAME/KEY: protein_bind
<222> LOCATION: (1)..(13)
<223> OTHER INFORMATION: Oligonucleotide containing mutated AloI
      recognition sequence and HindIII recognition sequence
<220> FEATURE:
<221> NAME/KEY: misc_feature
<222> LOCATION: (9)..(9)
<223> OTHER INFORMATION: n is A, C, G or T

<400> SEQUENCE: 45
ggaagcttng tta                                                      13

<210> SEQ ID NO 46
<211> LENGTH: 13
<212> TYPE: DNA
<213> ORGANISM: Artificial Sequence
<220> FEATURE:
<223> OTHER INFORMATION: Oligonucleotide containing mutated AloI
      recognition sequence and HindIII recognition sequence
<220> FEATURE:
<221> NAME/KEY: protein_bind
<222> LOCATION: (1)..(13)
<223> OTHER INFORMATION: Oligonucleotide containing mutated AloI
      recognition sequence and HindIII recognition sequence
<220> FEATURE:
<221> NAME/KEY: misc_feature
<222> LOCATION: (9)..(9)
<223> OTHER INFORMATION: n is A, C, G or T

<400> SEQUENCE: 46
ggaagcttng ttg                                                      13

<210> SEQ ID NO 47
<211> LENGTH: 13
<212> TYPE: DNA
<213> ORGANISM: Artificial Sequence
<220> FEATURE:
<223> OTHER INFORMATION: Oligonucleotide containing mutated AloI
      recognition sequence and HindIII recognition sequence
<220> FEATURE:
<221> NAME/KEY: protein_bind
<222> LOCATION: (1)..(13)
<223> OTHER INFORMATION: Oligonucleotide containing mutated AloI
      recognition sequence and HindIII recognition sequence
<220> FEATURE:
<221> NAME/KEY: misc_feature
<222> LOCATION: (9)..(9)
```

```
<223> OTHER INFORMATION: n is A, C, G or T

<400> SEQUENCE: 47
ggaagcttng ttt                                                          13

<210> SEQ ID NO 48
<211> LENGTH: 42
<212> TYPE: DNA
<213> ORGANISM: Artificial Sequence
<220> FEATURE:
<223> OTHER INFORMATION: Eco57I T862N cleavage after reaction with T4
      DNA polymerase

<400> SEQUENCE: 48
taatagactg gatggaggcg ctggagccgg tgagcgtggg tc                           42

<210> SEQ ID NO 49
<211> LENGTH: 20
<212> TYPE: DNA
<213> ORGANISM: Artificial Sequence
<220> FEATURE:
<223> OTHER INFORMATION: Eco57I T862N cleavage on the opposite DNA
      strand after reaction with T4 DNA polymerase

<400> SEQUENCE: 49
cccacgctca ccggctccag                                                   20

<210> SEQ ID NO 50
<211> LENGTH: 44
<212> TYPE: DNA
<213> ORGANISM: Artificial Sequence
<220> FEATURE:
<223> OTHER INFORMATION: Eco57I T862N cleavage after reaction with T4
      DNA polymerase

<400> SEQUENCE: 50 tcccttttt gcggcatttt gctgaagatc agttgggtgc acga                         44

<210> SEQ ID NO 51
<211> LENGTH: 21
<212> TYPE: DNA
<213> ORGANISM: Artificial Sequence
<220> FEATURE:
<223> OTHER INFORMATION: Eco57I T862N cleavage on the opposite DNA
      strand after reaction with T4 DNA polymerase

<400> SEQUENCE: 51
gtgcacccaa ctgatcttca g                                                 21
```